(12) United States Patent
Kárpáti et al.

(10) Patent No.: US 10,383,865 B2
(45) Date of Patent: *Aug. 20, 2019

(54) PHARMACEUTICAL COMBINATION COMPOSITION COMPRISING COMPLEX FORMULATIONS OF IVACAFTOR AND LUMACAFTOR AND THEIR SALTS AND DERIVATIVES, PROCESS FOR THEIR PREPARATION THEREOF AND PHARMACEUTICAL COMPOSITIONS CONTAINING THEM

(71) Applicant: Druggability Technologies IP Holdco Limited, Swatar (MT)

(72) Inventors: Richárd Balázs Kárpáti, Tatabánya (HU); Gergo Patyi, Vecsés (HU); Orsolya Basa-Dénes, Eger (HU); Betti Szabóné Ordasi, Budapest (HU); Erzsébet Réka Angi, Nagykovácsi (HU); Hristos Glavinas, Szeged (HU); Genovéva Filipcsei, Budapest (HU)

(73) Assignee: Druggability Technologies IP Holdco Limited, Msida (MT)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,253

(22) Filed: Apr. 25, 2017

(65) Prior Publication Data
US 2017/0304287 A1 Oct. 26, 2017

Related U.S. Application Data

(60) Provisional application No. 62/327,152, filed on Apr. 25, 2016.

(51) Int. Cl.
*A61K 47/58* (2017.01)
*A61K 9/14* (2006.01)
(Continued)

(52) U.S. Cl.
CPC .............. *A61K 31/47* (2013.01); *A61K 9/009* (2013.01); *A61K 9/0095* (2013.01); *A61K 9/10* (2013.01);
(Continued)

(58) Field of Classification Search
None
See application file for complete search history.

(56) References Cited

U.S. PATENT DOCUMENTS

| 6,969,529 B2 | 11/2005 | Bosch |
| 7,495,103 B2 | 2/2009 | Hadida-Ruah |

(Continued)

FOREIGN PATENT DOCUMENTS

| CN | 104725314 | 6/2015 |
| EP | 2819670 | 1/2015 |

(Continued)

OTHER PUBLICATIONS

CoNCERT, Product Innovation. Patient Impact, Jeffries Healthcare Conference, Roger Tung, Ph.D., President and CEO, Jun. 3, 2015, 20 pages.

(Continued)

*Primary Examiner* — Ernst V Arnold
*Assistant Examiner* — Kyung S Chang
(74) *Attorney, Agent, or Firm* — Dennis A. Bennett; Brock D. Levin; Lauren L. Stevens

(57) ABSTRACT

Pharmaceutical combinations comprise stable complexes with controlled particle size, increased apparent solubility and increased dissolution rate comprising as active compound Ivacaftor and Lumacaftor, their salts, or derivatives thereof, which are useful in the treatment of cystic fibrosis transmembrane conductance regulator (CFTR) mediated disease. More specifically, the pharmaceutical composition comprising the complexes possesses instantaneous redis-
(Continued)

| | PAMPA permeability (*10-6 cm/s) | | | | | |
|---|---|---|---|---|---|---|
| | Average | | | STD | | |
| | Water | FaSSIF | FeSSIF | H2O | FaSSIF | FeSSIF |
| Complex Ivacaftor formulation in pharmaceutical combination composition prepared by powder blending | 0.41 | 0.296 | 0.292 | 0 | 0.016 | 0.009 |
| Complex Ivacaftor formulation in pharmaceutical combination composition prepared by powder blending. Stored at 40 °C for 6 months | 0.354 | 0.407 | 0.464 | 0.065 | 0.061 | 0.084 |
| Complex Lumacaftor formulation in pharmaceutical combination composition prepared by powder blending | 5.106 | 5.811 | 4.937 | 0 | 0.226 | 0.122 |
| Complex Lumacaftor formulation in pharmaceutical combination composition prepared by powder blending. Stored at 40 °C for 6 months | 1.732 | 3.976 | 3.548 | 0.1 | 0.185 | 0.56 |
| Complex Ivacaftor formulation in pharmaceutical combination composition prepared by spray-drying in combination | 0.413 | 0.384 | 0.434 | 0.033 | 0.005 | 0.058 |
| Complex Ivacaftor formulation in pharmaceutical combination composition prepared by spray-drying in combination. Stored at 40 °C for 2 months | 0.232 | 0.180 | 0.224 | 0.042 | 0.005 | 0.055 |
| Complex Lumacaftor formulation in pharmaceutical combination composition prepared by spray-drying in combination | 3.491 | 6.681 | 5.484 | 0.157 | 0.247 | 0.114 |
| Complex Lumacaftor formulation in pharmaceutical combination composition prepared by spray-drying in combination. Stored at 40 °C for 2 months | 2.216 | 4.226 | 3.819 | 0.121 | 0.081 | 0.557 | persibility, increased apparent solubility and permeability, no observable food effect which deliver the opportunity of precise dosing and ease of administration of the reconstituted complex in solution form. Further disclosed are methods of formulating and manufacturing the complexes, pharmaceutical compositions containing the complexes, and methods of treatment using the complexes and their pharmaceutical compositions.

11 Claims, 28 Drawing Sheets

(51) Int. Cl.
  *A61K 9/10* (2006.01)
  *A61K 47/10* (2017.01)
  *A61K 9/16* (2006.01)
  *A61K 45/06* (2006.01)
  *A61K 31/47* (2006.01)
  *A61K 31/443* (2006.01)
  *A61K 9/00* (2006.01)

(52) U.S. Cl.
  CPC ............ *A61K 9/146* (2013.01); *A61K 9/1635* (2013.01); *A61K 9/1641* (2013.01); *A61K 31/443* (2013.01); *A61K 45/06* (2013.01); *A61K 47/10* (2013.01); *A61K 47/58* (2017.08)

(56) References Cited

U.S. PATENT DOCUMENTS

| | | |
|---|---|---|
| 8,324,242 B2 | 12/2012 | Ruah |
| 8,354,427 B2 | 1/2013 | Van Goor |
| 8,507,534 B2 | 8/2013 | Keshavarz-Shokri |
| 8,653,103 B2 | 2/2014 | Keshavarz-Shokri |
| 8,716,338 B2 | 5/2014 | Young |
| 8,754,224 B2 | 6/2014 | Hurter |
| 8,846,718 B2 | 9/2014 | Keshavarz-Shokri |
| 8,883,206 B2 | 11/2014 | Dokou |
| 8,993,600 B2 | 3/2015 | Hadida Ruah |
| 9,181,192 B2 | 11/2015 | Morgan |
| 10,206,915 B2 | 2/2019 | Kárpáti |
| 2013/0085158 A1 | 4/2013 | Keshavarz-Shokri |
| 2013/0296379 A1 | 11/2013 | Keshavarz-Shokri |
| 2014/0163068 A1 | 6/2014 | Verwijs |
| 2014/0221424 A1 | 8/2014 | Zha |
| 2014/0221430 A1 | 8/2014 | Keshavarz-Shokri |
| 2014/0255483 A1 | 9/2014 | Dokou |
| 2015/0010628 A1 | 1/2015 | Dokou |
| 2015/0024047 A1 | 1/2015 | Dokou |
| 2015/0132388 A1 | 5/2015 | Angi |
| 2015/0140094 A1 | 5/2015 | Verwijs |
| 2015/0182517 A1 | 7/2015 | Alargova |
| 2015/0196539 A1 | 7/2015 | Keshavarz-Shokri |
| 2015/0246031 A1 | 9/2015 | Dokou |
| 2016/0039800 A1 | 2/2016 | Young |
| 2017/0326121 A1 | 11/2017 | Kárpáti |
| 2017/0326129 A1 | 11/2017 | Kárpáti |

FOREIGN PATENT DOCUMENTS

| | | |
|---|---|---|
| EP | 2826776 | 1/2015 |
| EP | 2872122 | 5/2015 |
| JP | 2014097964 | 5/2014 |
| WO | 2009076141 | 6/2009 |
| WO | 2011127241 | 10/2011 |
| WO | 2011127290 | 10/2011 |
| WO | 2013112804 | 8/2013 |
| WO | 2014118805 | 8/2014 |
| WO | 2014125506 | 8/2014 |
| WO | 2014135096 | 9/2014 |
| WO | 2015070336 | 5/2015 |
| WO | 2015071836 | 5/2015 |
| WO | 2015071837 | 5/2015 |
| WO | 2015071841 | 5/2015 |
| WO | 2015073231 | 5/2015 |
| WO | 2015121836 | 8/2015 |
| WO | 2015160787 | 10/2015 |
| WO | 2015175773 | 11/2015 |

OTHER PUBLICATIONS

Morgan, A. et al., Design and Synthesis of Deuterated Analogs of Ivacaftor With Enhanced Pharmacokinetic Properties, CoNCERT Pharmaceuticals Inc., 2012, Poster, 1 page.
Uttamsingh, V. et al., CTP-656 Multiple Dose Pharmacokinetic Profile Continues to Support a Once-Daily Potentiator for Cystic Fibrosis Patients With Gating Mutations, CoNCERT Pharmaceuticals, Inc., #224, Poster, 1 page.
Khatry, et al., "Surface and Solid Dispersion—A Review", International Journal of Pharmaceutical Sciences and Nanotechnology, 6(1): , (2013), (Abstract only).
Thakur, et al., "A Review on Solid Dispersions", World Journal of Pharmacy and Pharmaceutical Sciences, 3(9):173-87, (2014).
U.S. Appl. No. 15/496,246; Non-Final Office Action dated Aug. 23, 2018; 19 pages.
Wainright, et al., "Lumacaftor-Ivacaftor in Patients with Cystic Fibrosis Homozygous for Phe508del CFTR", NEJM, 373:220-31, (2015).
International Application No. PCT/IB2017/052372; International Search Report and Written Opinion of the International Searching Authority, dated Sep. 8, 2017; 11 pages.
Rask, M. et al., "Influence of PVP/VA Copolymer Solubility", European Journal of Pharmaceutical Sciences, 85:10-7, (2016).
Rosebraugh, C., "Highlights of Prescribing Information. These highlights do not include all the information needed to use ORKAMBI safely and effectively. See full prescribing information for ORKAMBI", Retrieved from the Internet: https://www.accessdata.fda.gov/drugsatfda_docs/label/2015/206038Orig1s000lbl.pdf; (Jul. 1, 2015).
U.S. Appl. No. 15/496,239; Non-Final Office Action dated Jan. 30, 2018; 8 pages.
U.S. Appl. No. 15/496,239; Examiner Initiated Interview Summary dated Sep. 26, 2018; 1 page.
U.S. Appl. No. 15/496,239; Notice of Allowance dated Sep. 26, 2018; 9 pages.
U.S. Appl. No. 16/229,235; Application as filed, dated Dec. 21, 2018; 59 pages.
U.S. Appl. No. 15/496,246; Final Office Action dated Jan. 11, 2019; 10 pages.

Figure 1

| Composition | Solution 1 (S): Solution 2 (AS) ratio | $V_S, V_{AS}$ (mL/min) | T (°C) | Appearance |
|---|---|---|---|---|
| Mass ratio of Ivacaftor/complexation agent/poloxamer 338/pharmaceutically acceptable excipient = 1:3:2:1 | 1:1 | 2.5 | 25 | Inhomogeneous solution |
| | | 5 | 25 | Inhomogeneous solution |
| | | 10 | 25 | Inhomogeneous solution |
| | | 20 | 25 | Inhomogeneous solution |
| | | 30 | 25 | Inhomogeneous solution |
| | | 40 | 25 | Homogeneous colloid solution |
| | | 20 | 40 | Inhomogeneous solution |
| | | 30 | 40 | Inhomogeneous solution |
| | | 40 | 40 | Homogeneous colloid solution |
| | | 40 | 20 | Homogeneous colloid solution |
| | | 40 | 30 | Homogeneous colloid solution |
| | | 40 | 50 | Inhomogeneous solution |

Figure 2

| Composition | Lumacaftor content of the dispersions (mg/mL) | Ivacaftor content of the dispersions (mg/mL) | Apparent solubility of Lumacaftor (mg/mL) | Apparent solubility of Ivacaftor (mg/mL) |
|---|---|---|---|---|
| Crystalline Lumacaftor | 1 | - | 0.000 | - |
| Crystalline Ivacaftor | - | 1 | - | 0.000 |
| Complex Lumacaftor | 1 | - | 0.950 | - |
|  | 10 | - | 9.839 | - |
|  | 20 | - | 14.913 | - |
| Complex Ivacaftor formulation | - | 1 | - | 0.991 |
|  | - | 2.5 | - | 2.356 |
|  | - | 5 | - | 4.924 |
|  | - | 10 | - | 9.463 |
|  | - | 20 | - | 18.474 |
| Pharmaceutical combination composition prepared by powder blending | 20 | 12.5 | 19.949 | 11.319 |
|  | 10 | 6.25 | 9.591 | 5.755 |
|  | 5 | 3.15 | 4.697 | 2.844 |
|  | 1 | 0.625 | 1.009 | 0.612 |
| Pharmaceutical combination composition prepared by spray-drying in combination | 20 | 12.5 | 19.266 | 12.047 |
|  | 10 | 6.25 | 8.910 | 5.540 |
|  | 5 | 3.15 | 4.825 | 3.010 |
|  | 1 | 0.625 | 0.965 | 0.597 |

Figure 4

|  | Time (min) | | |
| --- | --- | --- | --- |
|  | 5 | 15 | 30 |
| Dissolved Ivacaftor from pharmaceutical combination composition prepared by powder blending | 88.1% | 95.1% | 96.7% |
| Dissolved Lumacaftor from pharmaceutical combination composition prepared by powder blending | 86.0% | 93.8% | 95.1% |
| Dissolved Ivacaftor from pharmaceutical combination composition prepared by spray drying in combination | 89.6% | 95.9% | 95.6% |
| Dissolved Lumacaftor from pharmaceutical combination composition prepared by spray drying in combination | 90.1% | 97.8% | 97.8% |
| Dissolved Ivacaftor from Orkambi equivalent powder blend | 0.0% | 0.0% | 0.0% |
| Dissolved Lumacaftor from Orkambi equivalent powder blend | 2.6% | 2.1% | 3.6% |

Figure 8

| Storage condition | Time (month) | Medium | PAMPA permeability ($*10^{-6}$ cm/s) | |
|---|---|---|---|---|
| | | | Complex Ivacaftor | Complex Lumacaftor |
| Right after the production | 0 | FaSSIF | 0.5487 | 6.4690 |
| | | FeSSIF | 0.6409 | 2.9954 |
| Room temperature | 6 | FaSSIF | 0.4871 | 5.9291 |
| | | FeSSIF | 0.5491 | 4.5905 |
| 40 °C/75% relative humidity | 6 | FaSSIF | 0.5502 | 4.2427 |
| | | FeSSIF | 0.5568 | 3.3242 |

Figure 9

|  | PAMPA permeability (*10-6 cm/s) | | | | | |
|---|---|---|---|---|---|---|
|  | Average | | | STD | | |
|  | Water | FaSSIF | FeSSIF | H2O | FaSSIF | FeSSIF |
| Complex Ivacaftor formulation in pharmaceutical combination composition prepared by powder blending | 0.41 | 0.296 | 0.292 | 0 | 0.016 | 0.009 |
| Complex Ivacaftor formulation in pharmaceutical combination composition prepared by powder blending. Stored at 40 °C for 6 months | 0.354 | 0.407 | 0.464 | 0.065 | 0.061 | 0.084 |
| Complex Lumacaftor formulation in pharmaceutical combination composition prepared by powder blending | 5.106 | 5.811 | 4.937 | 0 | 0.226 | 0.122 |
| Complex Lumacaftor formulation in pharmaceutical combination composition prepared by powder blending. Stored at 40 °C for 6 months | 1.732 | 3.976 | 3.548 | 0.1 | 0.185 | 0.56 |
| Complex Ivacaftor formulation in pharmaceutical combination composition prepared by spray-drying in combination | 0.413 | 0.384 | 0.434 | 0.033 | 0.005 | 0.058 |
| Complex Ivacaftor formulation in pharmaceutical combination composition prepared by spray-drying in combination. Stored at 40 °C for 2 months | 0.232 | 0.180 | 0.224 | 0.042 | 0.005 | 0.055 |
| Complex Lumacaftor formulation in pharmaceutical combination composition prepared by spray-drying in combination | 3.491 | 6.681 | 5.484 | 0.157 | 0.247 | 0.114 |
| Complex Lumacaftor formulation in pharmaceutical combination composition prepared by spray-drying in combination. Stored at 40 °C for 2 months | 2.216 | 4.226 | 3.819 | 0.121 | 0.081 | 0.557 |

Figure 17

| Composition | Ivacaftor content of the dispersions (mg/mL) | Apparent solubility (mg/mL) |
|---|---|---|
| Crystalline Ivacaftor | 1 | 0 |
| Physical mixture of Ivacaftor, Luviskol VA 64, poloxamer (Poloxamer 338 - Pluronic F108) and sodium-lauryl-sulfate | 3 | 0.043 |
| Crystalline Ivacaftor in 3 mg/mL sodium-lauryl-sulfate aqueous solution | 3 | 0.017 |
| Amorphous Ivacaftor in 3 mg/mL sodium-lauryl-sulfate aqueous solution | 3 | 0.077 |
| Solid dispersion | 1 | 0.071 |
| Complex Ivacaftor formulation | 1 | 0.991 |
| Complex Ivacaftor formulation | 20 | 18.474 |

Figure 19

| Reconstituted/redispersed compositions | | API concentration in reconstituted/redispersed solution (mg/mL) | | $D_{10}$ (nm) | $D_{50}$ (nm) | $D_{90}$ (nm) | PDI |
|---|---|---|---|---|---|---|---|
| Lumacaftor | Ivacaftor | Lumacaftor | Ivacaftor | | | | |
| Complex Lumacaftor | Complex Ivacaftor | 1 | 0.625 | 95.78 | 133 | 250 | 0.1324 |
| Milled composition of complex Lumacaftor | Milled composition of solid dispersion of Ivacaftor | 1 | 0.625 | 250 | 458 | 678 | 0.1119 |
| Complex Lumacaftor | Complex Ivacaftor | 1 | 1 | 95.1 | 171 | 336 | 0.2842 |
| Milled crystalline Lumacaftor | Solid dispersion of Ivacaftor | 1 | 0.625 | Not applicable: visible aggregates | | | |
| Milled crystalline Lumacaftor | Milled composition of solid dispersion of Ivacaftor | 1 | 0.625 | Not applicable: visible aggregates | | | |
| - | Milled composition of complex of Ivacaftor | 0 | 1 | 252 | 585 | 914 | |
| Milled composition of complex Lumacaftor | - | 1 | 0 | 224 | 431 | 798 | |
| - | Complex Ivacaftor | 0 | 1 | 149 | 324 | 577 | |
| Complex Lumacaftor | - | 1 | 0 | 143 | 205 | 282.4 | |

Figure 20

| Composition | Lumacaftor content of the dispersions (mg/mL) | Apparent solubility (mg/mL) |
|---|---|---|
| Crystalline Lumacaftor | 1 | 0 |
| Physical mixture | 1 | 0.032 |
| Ball milled crystalline Lumacaftor | 1 | 0.003 |
| Ball milled composition of complex Lumacaftor | 1 | 0.125 |
| Complex Lumacaftor | 1 | 0.950 |
| Complex Lumacaftor | 20 | 14.913 |

Figure 21

| Composition | PAMPA permeability ($*10^{-6}$ cm/s) |
|---|---|
| Crystalline Lumacaftor | 0.344 |
| Physical mixture | 0.226 |
| Ball milled crystalline Lumacaftor | 0.288 |
| Ball milled composition of complex Lumacaftor | 1.200 |
| Complex Lumacaftor formulation | 4.651 |

Figure 24

| Tested composition | | PAMPA permeability ($*10^{-6}$ cm/s) | | |
|---|---|---|---|---|
| | | Water | FaSSIF | FeSSIF |
| Orkambi equivalent pharmaceutical combination composition prepared by powder blending | Complex Ivacaftor formulation | 0.655 | 0.683 | 0.639 |
| | Complex Lumacaftor formulation | 4.073 | 4.651 | 3.315 |
| Orkambi equivalent pharmaceutical combination composition prepared by spray-drying in combination | Complex Ivacaftor formulation | 0.413 | 0.384 | 0.434 |
| | Complex Lumacaftor formulation | 3.491 | 6.681 | 5.484 |
| Orkambi equivalent ball milled physical mixture | Ball milled composition of complex Ivacaftor | 0.741 | 0.592 | 0.877 |
| | Ball milled composition of complex Ivacaftor | 1.180 | 1.200 | 1.338 |
| Orkambi equivalent mixture of milled Lumacaftor and Ivacaftor solid dispersion mixture | Ivacaftor Solid dispersion | 0.141 | 0.128 | 0.266 |
| | Ball milled crystalline Lumacaftor | 0.439 | 0.288 | 0.385 |
| Orkambi equivalent mixture of crystalline Ivacaftor and Lumacaftor | Crystalline Ivacaftor | 0.115 | 0.109 | 0.155 |
| | Crystalline Lumacaftor | 0.374 | 0.344 | 0.298 |
| Orkambi equivalent powder blend of complex Ivacaftor and complex Lumacaftor compositions | Physical mixture of complex Ivacaftor composition | 0.186 | 0.171 | 0.175 |
| | Physical mixture of complex Lumacaftor composition | 0.195 | 0.251 | 0.226 |

Figure 26

| Test item | Feeding condition | $C_{max}$(ng/ml) | $C_{24h}$(ng/ml) | AUC (ng/ml*h) |
|---|---|---|---|---|
| Complex Ivacaftor formulation | fed | 1620 ± 405 | 1230 ± 364 | 41652 ± 11758 |
| Complex Ivacaftor formulation | fasted | 1955 ± 359 | 1050 ± 86 | 36728 ± 4947 |
| Literature reference data* | fasted | 2255 ± 748 | 774 ± 230 | 29448 ± 8464 |

*http://www.concertpharma.com/news/documents/ISSX2013DIvacaftor.pdf

PHARMACEUTICAL COMBINATION COMPOSITION COMPRISING COMPLEX FORMULATIONS OF IVACAFTOR AND LUMACAFTOR AND THEIR SALTS AND DERIVATIVES, PROCESS FOR THEIR PREPARATION THEREOF AND PHARMACEUTICAL COMPOSITIONS CONTAINING THEM

This application claims the benefit of priority to U.S. provisional application No. 62/327,152, filed Apr. 25, 2016, the disclosure of which is hereby incorporated by reference as if written herein in its entirety.

FIELD OF THE INVENTION

Disclosed herein are stable complexes with controlled particle size, increased apparent solubility and increased dissolution rate comprising as active compound Ivacaftor and Lumacaftor, or salts or derivatives thereof, which are useful in the treatment of cystic fibrosis transmembrane conductance regulator (CFTR) mediated disease. More specifically, the pharmaceutical composition comprising the complexes possess instantaneous redispersibility, increased apparent solubility and permeability compared to KALYDECO® and ORKAMBI® like formulations, no observable food effect which deliver the opportunity of precise dosing and ease of administration of the reconstituted complex in solution form. Further disclosed are methods of formulating and manufacturing said complexes, pharmaceutical compositions comprising said complexes, and methods of treatment using said complexes and compositions.

BACKGROUND OF THE INVENTION

The active ingredient in KALYDECO® tablets is Ivacaftor, which has the following chemical name: N-(2,4-di-tert-butyl-5-hydroxyphenyl)-1,4-dihydro-4oxoquinoline-3-carboxamide. Its molecular formula is $C_{24}H_{28}N_2O_3$ and its molecular weight is 392.49. Ivacaftor has the following structural formula:

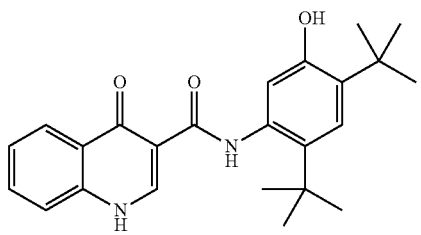 [SMILES: CC(C)(C)c1cc(C(C)(C)C)c(NC(=O)c2c[nH]c3ccccc3c2=O)cc1O]

Ivacaftor is a white to off-white powder that is practically insoluble in water (<0.05 microgram/mL). Due to poor aqueous solubility, extensive formulation efforts were required and resulted in a spray-dried dispersion of Ivacaftor suitable for oral administration. KALYDECO® containing the spray-dried dispersion of Ivacaftor is available as a light blue capsule-shaped, film-coated tablet for oral administration containing 150 mg of Ivacaftor. Each tablet contains the inactive ingredients colloidal silicon dioxide, croscarmellose sodium, hypromellose acetate succinate, lactose monohydrate, magnesium stearate, microcrystalline cellulose, and sodium lauryl sulfate. The tablet film coat contains carnauba wax, FD&C Blue #2, PEG 3350, polyvinyl alcohol, talc, and titanium dioxide. The printing ink contains ammonium hydroxide, iron oxide black, propylene glycol, and shellac.

Ivacaftor is a potentiator of the CFTR protein. The CFTR protein is a chloride channel present at the surface of epithelial cells in multiple organs. Ivacaftor facilitates increased chloride transport by potentiating the channel-open probability (or gating) of the CFTR protein.

After oral administration of a single 150 mg dose to healthy volunteers in a fed state, peak plasma concentrations ($t_{max}$) occurred at approximately 4 hours, and the mean (±SD) for AUC and $C_{max}$ were 10,600 (5260) ng*hr/mL and 768 (233) ng/mL, respectively. After every 12-hour dosing, steady-state plasma concentrations of Ivacaftor were reached by days 3 to 5, with an accumulation ratio ranging from 2.2 to 2.9.

The exposure of Ivacaftor increased approximately 2-to 4-fold when given with food containing fat. Therefore, KALYDECO® should be administered with fat-containing food. Examples of fat-containing foods include eggs, butter, peanut butter, and cheese pizza. The median (range) $t_{max}$ is approximately 4.0 (3.0; 6.0) hours in the fed state.

The mean apparent volume of distribution (Vz/F) of Ivacaftor after a single dose of 275 mg of KALYDECO® in the fed state was similar for healthy subjects and patients with CF. After oral administration of 150 mg every 12 hours for 7 days to healthy volunteers in a fed state, the mean (±SD) for apparent volume of distribution was 353 (122) L.

Ivacaftor is extensively metabolized in humans. In-vitro and clinical studies indicate that Ivacaftor is primarily metabolized by CYP3A. M1 and M6 are the two major metabolites of Ivacaftor in humans. M1 has approximately one-sixth the potency of Ivacaftor and is considered pharmacologically active. M6 has less than one-fiftieth the potency of Ivacaftor and is not considered pharmacologically active.

Following oral administration, the majority of Ivacaftor (87.8%) is eliminated in the feces after metabolic conversion. The major metabolites M1 and M6 accounted for approximately 65% of the total dose eliminated with 22% as M1 and 43% as M6. There was negligible urinary excretion of Ivacaftor as unchanged parent. The apparent terminal half-life was approximately 12 hours following a single dose. The mean apparent clearance (CL/F) of Ivacaftor was similar for healthy subjects and patients with CF. The CL/F (SD) for the 150 mg dose was 17.3 (8.4) L/hr in healthy subjects.

Lumacaftor is one of the active ingredients in ORKAMBI® tablets, which has the following chemical name: 3-[6-({[1-(2,2-difluoro-1,3-benzodioxol-5-yl)cyclopropyl]carbonyl}amino-3-methypyridin-2-yl]benzoic acid. The molecular formula for lumacaftor is $C_{24}H_{18}F_2N_2O_5$. The molecular weight for Lumacaftor is 452.41. The structural formula is:

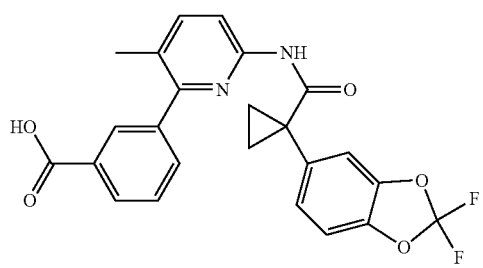 [SMILES: Cc1ccc(NC(=O)C2(c3ccc4c(c3)OC(F)(F)O4)CC2)nc1-c1cccc(C(=O)O)c1]

Lumacaftor is a white to off-white powder that is practically insoluble in water (0.02 mg/mL).

ORKAMBI® is available as a pink, oval-shaped, film-coated tablet for oral administration containing 200 mg of Lumacaftor and 125 mg of Ivacaftor. Each ORKAMBI® tablet contains 200 mg of Lumacaftor and 125 mg of Ivacaftor, and the following inactive ingredients: cellulose, microcrystalline; croscarmellose sodium; hypromellose acetate succinate; magnesium stearate; povidone; and sodium lauryl sulfate. The tablet film coat contains carmine, FD&C Blue #1, FD&C Blue #2, polyethylene glycol, polyvinyl alcohol, talc, and titanium dioxide. The printing ink contains ammonium hydroxide, iron oxide black, propylene glycol, and shellac.

Lumacaftor improves the conformational stability of F508del-CFTR, resulting in increased processing and trafficking of mature protein to the cell surface. In-vitro studies have demonstrated that Lumacaftor acts directly on the CFTR protein in primary human bronchial epithelial cultures and other cell lines harboring the F508del-CFTR mutation to increase the quantity, stability, and function of F508del-CFTR at the cell surface, resulting in increased chloride ion transport.

Following multiple oral dose administrations of Lumacaftor, the exposure of Lumacaftor increased roughly proportionally with dose from 50 to 1000 mg qd. In subjects with CF, the Lumacaftor $C_{max}$ and AUC also increases approximately proportional with the dose over the Lumacaftor 25 mg qd to 400 mg q12h dose range. The exposure of Lumacaftor increased approximately 1.6-to 2.0-fold when given with fat containing food. The median (range) time of the maximum concentration ($t_{max}$) is approximately 4.0 (2.0, 9.0) hours in the fed state.

Lumacaftor is approximately 99% bound to plasma proteins, primarily to albumin. After oral administration of 200 mg every 24 hours for 28 days to patients with cystic fibrosis (CF) in a fed state, the mean (±SD) for apparent volumes of distribution was 86.0 (69.8) L.

The half-life of Lumacaftor is approximately 26 hours in patients with CF. The typical apparent clearance, CL/F (CV), of Lumacaftor was estimated to be 238 L/hr (29.4%) for patients with CF.

Lumacaftor is not extensively metabolized in humans with the majority (51%) of Lumacaftor excreted unchanged in the feces. There was minimal elimination of Lumacaftor and its metabolites in urine (only 8.6% of total radioactivity was recovered in the urine with 0.18% as unchanged parent). In-vitro and in vivo data indicate that Lumacaftor is mainly metabolized via oxidation and glucuronidation.

Lumacaftor has low aqueous solubility and high permeability assessed via the colorectal adenocarcinoma (Caco-2) cell system. Although pH-dependent solubility was observed, the Lumacaftor drug substance is practically insoluble in water and buffer solutions of pH 1.0 to pH 8.0. Therefore, Lumacaftor is suggested to be a BCS Class 2 (low solubility/high permeability) compound.

Since Lumacaftor is considered a BCS class II, the drug substance was jet-milled early in development to reduce the particle size and potentially improve bioavailability. Based on these studies a control on Lumacaftor particle size in the drug substance specification was established.

Various formulations have been used in the development of Lumacaftor alone and in combination which includes suspension, capsules and tablets. Comparative exposure of the different formulations of Lumacaftor was seen in single dose studies in healthy volunteers. Exposure of the suspension is lower than that seen for capsules and tablets. Early clinical studies were conducted with the co-administration of both Ivacaftor and Lumacaftor. A cross-over study (007) was conducted to evaluate the relative bioavailability of the fixed dose combination tablet as compared to the separate tablets. The tablet and FDC appear to be bioequivalent, and the only parameter that did not meet standard bioequivalence criteria is the $C_{max}$ of Ivacaftor (GLSMR [90% CI]— 1.20 [1.09, 1.33]). However, for practical purposes this is acceptable and the PK results from tablet formulation can be considered applicable to the FDC as well.

When a single dose of Lumacaftor/Ivacaftor was administered with fat-containing foods, Lumacaftor exposure was approximately 2 times higher and Ivacaftor exposure was approximately 3 times higher than when taken in a fasting state.

Following multiple oral dose administration of Lumacaftor in combination with Ivacaftor, the exposure of Lumacaftor generally increased proportional to dose over the range of 200 mg every 24 hours to 400 mg every 12 hours. The median (range) $t_{max}$ of Lumacaftor is approximately 4.0 hours (2.0; 9.0) in the fed state.

Following multiple oral dose administration of Ivacaftor in combination with Lumacaftor, the exposure of Ivacaftor generally increased with dose from 150 mg every 12 hours to 250 mg every 12 hours. The median (range) $t_{max}$ of ivacaftor is approximately 4.0 hours (2.0; 6.0) in the fed state.

The main medical concerns surrounding the administration of Ivacaftor and Lumacaftor are related to the positive food effect both compounds exhibit which does not allow the precise administration of the current formulations. This is extensively true for pediatric patients where the current, fix dose tablet formulation does not allow the administration of the compound to children.

In order to overcome the problems associated with prior conventional formulations and available drug delivery systems containing Ivacaftor in combination with Lumacaftor, novel pharmaceutical composition comprising complex formulations of Ivacaftor, or salts or derivatives thereof, together with complexation agents and pharmaceutically acceptable excipients in combination with complex formulations of Lumacaftor, or salts or derivatives thereof, together with complexation agents and pharmaceutically acceptable excipients were prepared. Novel pharmaceutical compositions are characterized by instantaneous redispersibility, increased apparent solubility compared to KALYDECO® and ORKAMBI® like formulations, instantaneous dissolution, increased apparent permeability compared to KALYDECO® and ORKAMBI® like formulations that exhibits no food effect which allows the precise dosing the active ingredients.

BRIEF DESCRIPTION OF THE INVENTION

Disclosed herein is a pharmaceutical combination composition with improved physicochemical characteristics and enhanced biological performance comprising
  i. complex Ivacaftor formulation or its pharmaceutical composition;
  ii. complex Lumacator formulation or its pharmaceutical composition; and
  iii. optionally, one or more pharmaceutically acceptable excipients;
wherein said complex Ivacaftor formulation or its pharmaceutical composition comprising
  i. Ivacaftor, or a salt or derivative thereof;

ii. at least one complexing agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), copolymers of vinylpyrrolidone and vinyl acetate copolymer, poly(2-ethyl-2-oxazoline), polyvinylpyrrolidone, poly(maleic acid/methyl vinyl ether), polyvinyl caprolactam-polyvinyl acetate-polyethylene glycol graft copolymer, ethylene oxide/propylene oxide tetra functional block copolymer, and d-alpha tocopheryl polyethylene glycol 1000 succinate; and iii. optionally, one or more pharmaceutically acceptable excipients;

wherein said complex Lumacaftor formulation or its pharmaceutical composition comprises i. Lumacaftor, or a salt or derivative thereof;

ii. at least one complexation agent chosen from polyethylene glycol glycerides composed of mono-, di- and triglycerides and mono- and diesters of polyethylene glycol, hydroxypropylcellulose, poloxamers (copolymers of ethylene oxide and propylene oxide blocks), vinylpyrrolidone/vinyl acetate copolymer, poly(2-ethyl-2-oxazoline), polyvinylpyrrolidone, poly(maleic acid/methyl vinyl ether), polyvinyl caprolactam-polyvinyl acetate-polyethylene glycol graft copolymer, polyoxyl 15 hydroxystearate, ethylene oxide/propylene oxide tetra functional block copolymer, and d-alpha tocopheryl polyethylene glycol 1000 succinate; and iii. optionally, one or more pharmaceutically acceptable excipients;

wherein said complex formulations or their pharmaceutical combination compositions have particle size between 10 nm and 600 nm, and the said pharmaceutical combination composition possesses at least one of following features:

a) is instantaneously redispersable in physiological relevant media;

b) is stable in solid form and in colloid solution and/or dispersion;

c) complex Ivacaftor and complex Lumacaftor formulations or their pharmaceutical compositions have an apparent solubility in water of at least 1 mg/mL;

d) complex Ivacaftor and complex Lumacaftor formulations or their pharmaceutical compositions have a PAMPA permeability of at least $0.2*10^{-6}$ cm/s for Ivacaftor and $2*10^{-6}$ cm/s for Lumacaftor when dispersed in FaSSIF or FeSSIF biorelevant media, which does not decrease in time for at least 6 months;

e) has increased dissolution rate compared to KALYDECO® and ORKAMBI® like formulations: 80% of Ivacaftor and 80% of Lumacaftor released from the pharmaceutical composition within 5 minutes in biological relevant media;

f) exhibits no observable food effect; and g) has improved bioavailability both for Ivacaftor and Lumacaftor compared to KALYDECO® and ORKAMBI® like formulations.

In an embodiment, said complexes have particle size in the range between 10 nm and 400 nm.

In an embodiment, following multiple oral dose administration of Ivacaftor in combination with Lumacaftor, the exposure of Ivacaftor generally increased with dose from 150 mg every 12 hours to 250 mg every 12 hours. The median (range) $t_{max}$ of Ivacaftor is approximately 4.0 hours (2.0; 6.0) in the fed state.

In an embodiment, said complexes exhibit X-ray amorphous character in the solid form.

In an embodiment, said complexes or their pharmaceutical compositions or said pharmaceutical combination composition possess at least two of the properties described in a)-g).

In an embodiment, said complexes or their pharmaceutical compositions or pharmaceutical combination composition possess at least three of the properties described in a)-g).

In an embodiment, said pharmaceutical combination composition or said complexes or their pharmaceutical combination compositions possess instantaneous redispersibility, has an apparent solubility in water of at least 1 mg/mL, exhibits no observable food effect which deliver the opportunity of precise dosing and ease of administration of the reconstituted pharmaceutical combination composition in solution form.

In an embodiment, said complexes or their pharmaceutical combination compositions possess instantaneous redispersibility, have a PAMPA permeability of at least $0.2*10^{-6}$ cm/s for Ivacaftor and $2*10^{-6}$ cm/s for Lumacaftor when dispersed in water, FaSSIF or FeSSIF biorelevant media, which does not decrease in time for at least 6 month, exhibits no observable food effect which deliver the opportunity of precise dosing and ease of administration of the reconstituted pharmaceutical combination composition in solution form.

In an embodiment, the complexing agent of complex Ivacaftor formulation is a copolymer of vinylpyrrolidone and vinylacetate and optionally a poloxamer; and the complexing agent of complex Lumacaftor formulation is a copolymer of vinylpyrrolidone and vinylacetate.

In an embodiment, said pharmaceutically acceptable excipient of said complex Ivacaftor and complex Lumacaftor formulations is chosen from sodium deoxycholate, dioctyl sodium sulfosuccinate, sodium acetate, cetylpyridinium chloride, citric acid, meglumine and sodium lauryl sulfate.

In an embodiment, said pharmaceutically acceptable excipient is sodium lauryl sulfate.

In an embodiment, said pharmaceutical combination composition comprises i. complex Ivacaftor formulation;

ii. complex Lumacator formulation; and iii. optionally, pharmaceutically acceptable excipients;

wherein said complex Ivacaftor formulation comprising i. Ivacaftor;

ii. a complexing agent that is a copolymer of vinylpyrrolidone and vinylacetate; and iii. an excipient that is sodium lauryl sulfate;

wherein said complex Ivacaftor formulation is characterized by infrared (ATR) peaks 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$; and is characterized by Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$ and wherein said complex Lumacaftor formulation composition comprises i. Lumacaftor;

ii. a complexing agent that is copolymer of vinylpyrrolidone and vinylacetate; and iii. an excipient that is sodium lauryl sulfate;

wherein said complex Lumacaftor formulations is characterized by infrared (ATR) peaks at 635 $cm^{-1}$, 703 $cm^{-1}$, 747 $cm^{-1}$, 837 $cm^{-1}$, 1021 $cm^{-1}$, 1165 $cm^{-1}$, 1231 $cm^{-1}$, 1288

$cm^{-1}$, 1369 $cm^{-1}$, 1423 $cm^{-1}$, 1462 $cm^{-1}$, 1494 $cm^{-1}$, 1667 $cm^{-1}$ and 1731 $cm^{-1}$; and is characterized by Raman shifts at 553 $cm^{-1}$, 602 $cm^{-1}$, 635 $cm^{-1}$, 654 $cm^{-1}$, 747 $cm^{-1}$, 841 $cm^{-1}$, 899 $cm^{-1}$, 934 $cm^{-1}$, 1002 $cm^{-1}$, 1021 $cm^{-1}$, 1117 $cm^{-1}$, 1205 $cm^{-1}$, 1232 $cm^{-1}$, 1310 $cm^{-1}$, 1352 $cm^{-1}$, 1372 $cm^{-1}$, 1428 $cm^{-1}$, 1444 $cm^{-1}$, 1497 $cm^{-1}$, 1592 $cm^{-1}$, 1609 $cm^{-1}$, 1677 $cm^{-1}$ and 1737 $cm^{-1}$.

In an embodiment, said complex Ivacaftor formulation further comprises a poloxamer.

In an embodiment, said pharmaceutical combination composition comprises of 50 to 300 mg Ivacaftor equivalent complex Ivacaftor formulation in combination with 25 to 250 mg Lumacaftor equivalent complex Lumacaftor formulation.

In an embodiment, said pharmaceutical combination composition comprises complex Ivacaftor formulation, or its pharmaceutical composition, and complex Lumacaftor formulation, or its pharmaceutical composition, in a total amount ranging from about 10.0 weight % to 100.0 weight % based on the total weight of the pharmaceutical composition.

In an embodiment, said pharmaceutical combination composition comprises complex Ivacaftor formulation, or its pharmaceutical composition, and complex Lumacaftor formulation, or its pharmaceutical composition, in a total amount ranging from about 50.0 weight % to 100.0 weight % based on the total weight of the pharmaceutical composition.

In an embodiment, said pharmaceutical combination composition has an increased dissolution rate compared to KALYDECO® and ORKAMBI® like formulations.

Disclosed herein is a process for the preparation of the complexes of Ivacaftor, said process comprising the steps of mixing a pharmaceutically acceptable solution containing Ivacaftor and at least one complexing agent which is a copolymer of vinylpyrrolidone and vinylacetate with an aqueous solution containing at least one pharmaceutically accepted excipient which is sodium lauryl sulfate.

In an embodiment, said process further comprises mixing a second complexing agent which is a poloxamer.

Disclosed herein is a process for the preparation of the complexes of Lumacaftor, said process comprising the step of mixing a pharmaceutically acceptable solution containing Lumacaftor, and complexing agent which is a copolymer of vinylpyrrolidone and vinylacetate with an aqueous solution containing at least one pharmaceutically accepted excipient which is sodium lauryl sulfate.

Disclosed herein is a process for the preparation of the complexes of Ivacaftor and Lumacaftor, said processes comprising the step of mixing a pharmaceutically acceptable solution containing Ivacaftor and Lumacaftor, and complexing agent which is a copolymer of vinylpyrrolidone and vinylacetate with an aqueous solution containing at least one pharmaceutically accepted excipient which is sodium lauryl sulfate.

In an embodiment, said processes are performed in a continuous flow instrument.

In an embodiment, said continuous flow instrument is a microfluidic flow instrument.

In an embodiment, said pharmaceutically acceptable solvent of said pharmaceutically acceptable solution is chosen from water, methanol, ethanol, isopropanol, n-propanol, acetone, acetonitrile, dimethyl-sulfoxide, tetrahydrofuran, or combinations thereof.

In an embodiment, said pharmaceutically acceptable solvent of said pharmaceutically acceptable solution is methanol, tetrahydrofuran, or combinations thereof.

In an embodiment, said pharmaceutically acceptable solvents are miscible with each other and the aqueous solution; and said aqueous solution comprises 0.1 to 99.9% weight of the final solution.

Disclosed herein is a pharmaceutical combination composition comprising the pharmaceutical composition together with one or more pharmaceutically acceptable carriers.

In an embodiment, said pharmaceutical composition is suitable for oral, pulmonary, rectal, colonic, parenteral, intracisternal, intravaginal, intraperitoneal, ocular, otic, local, buccal, nasal, or topical administration.

In an embodiment, said pharmaceutical composition is suitable for oral administration.

In an embodiment, said pharmaceutical combination composition comprising the pharmaceutical composition comprises fast dissolving granules of the complex formulations.

In an embodiment, said fast dissolving granules are suitable for the preparation of sachet dosage form.

Disclosed herein is said complex for use in the treatment of CFTR mediated diseases.

In an embodiment, said CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

Disclosed herein is a method of treatment of CFTR mediated diseases comprising administration of a therapeutically effective amount of a pharmaceutical combination composition or a pharmaceutical composition.

In an embodiment, said pharmaceutical composition further comprises one or more additional active agents.

In an embodiment, said additional active agent chosen from agents used for the treatment of CFTR mediated diseases.

DESCRIPTION OF THE INVENTION

Disclosed herein is a pharmaceutical combination composition comprising a mixture of:
a) a stable complex Ivacaftor formulation;
b) a stable complex Lumacaftor formulation; and
c) optionally, pharmaceutically acceptable excipients.

In some embodiments, the pharmaceutical combination composition may additionally include one or more pharmaceutically acceptable excipients, auxiliary materials, carriers, active agents or combinations thereof.

In an embodiment, said pharmaceutical combination composition is suitable for oral administration.

In some embodiment, said pharmaceutical combination composition is suitable for oral administration as liquid dispersible granules in a sachet form.

In some embodiments, the daily human dose of said pharmaceutical combination composition can be adjusted based on the body weight by administering the pharmaceutical composition in the required amount.

In an embodiment, said pharmaceutical combination composition can be administered orally from the age of 0 (birth).

In an embodiment, said complex formulations and said pharmaceutical composition are for use in the manufacture of a medicament for the treatment of CFTR mediated diseases.

In an embodiment, said complex formulations and said pharmaceutical composition is used for the treatment of CFTR mediated diseases.

In an embodiment, said CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In an embodiment, a method of treatment of CFTR mediated diseases comprises administration of a therapeutically effective amount of complex formulations or their pharmaceutical combination compositions as described herein.

In an embodiment, said pharmaceutical composition further comprise one or more additional active agents.

In an embodiment, said additional active agent is chosen from agents used for the treatment of CFTR mediated diseases.

In an embodiment said pharmaceutical composition comprising complex Ivacaftor formulation in combination with complex Lumacaftor formulation and optionally further pharmaceutically acceptable excipients characterized in that it possesses at least one of the following properties:
a) is instantaneously redispersable in physiological relevant media;
b) is stable in solid form and in colloid solution and/or dispersion;
c) complex Ivacaftor and/or complex Lumacaftor formulations have an apparent solubility in water of at least 1 mg/mL;
d) complex Ivacaftor and/or complex Lumacaftor formulation have a PAMPA permeability of at least $0.2*10^{-6}$ cm/s for Ivacaftor and $2*10^{-6}$ cm/s for Lumacaftor when dispersed in FaSSIF or FeSSIF biorelevant media, which does not decrease in time for at least 6 month;
e) has increased dissolution rate: 80% of Ivacaftor and 80% of Lumacaftor released from the pharmaceutical composition within 5 minutes in biological relevant media;
f) exhibits no observable food effect; and
g) has increased bioavailability both for Ivacaftor and Lumacaftor compared to KALYDECO® and ORKAMBI® like formulations.

The complex Ivacaftor formulation comprises Ivacaftor; a complexing agent which is a copolymer of vinylpyrrolidone and vinylacetate; and sodium lauryl sulfate as a pharmaceutically acceptable excipient; said complexes characterized in that they possess at least one of the following properties:
a) is instantaneously redispersable in physiological relevant media;
b) is stable in solid form and in colloid solution and/or dispersion;
c) has an apparent solubility in water of at least 1 mg/mL;
d) has a PAMPA permeability of at least $0.2*10^{-6}$ cm/s when dispersed in FaSSIF or FeSSIF biorelevant media, which does not decrease in time for at least 6 month; and
e) exhibits no observable food effect.

In an embodiment, said Ivacafotr complex further comprises a poloxamer.

In an embodiment, said Ivacaftor complex possesses at least two of the properties described in a)–e).

In an embodiment, said Ivacaftor complex possesses at least three of the properties described in a)–e).

Ivacaftor formulations possess instantaneous redispersibility, increased apparent solubility and permeability compared to KALYDECO® and ORKAMBI® like formulations, no observable food effect which deliver the opportunity of precise dosing and ease of administration of the reconstituted complex in solution form.

The expression Ivacaftor is generally used for Ivacaftor, or its salts or its derivatives.

In an embodiment, said complexation agent used in the Ivacaftor complex is a copolymer of vinylpyrrolidone and vinylacetate, a poloxamer, or combinations thereof.

In an embodiment, said complexation agent used in the Ivacaftor complex as is a copolymer of vinylpyrrolidone and vinylacetate.

In an embodiment, said copolymer of vinylpyrrolidone and vinylacetate has a 60:40 weight ratio of vinylpyrrolidone:vinyl acetate monomers.

In an embodiment, said poloxamer is poloxamer 338.

In an embodiment, said poloxamer is poloxamer 407.

In an embodiment, said pharmaceutically acceptable excipient is sodium lauryl sulfate.

In an embodiment, said complexation agent is a combination of a copolymer of vinylpyrrolidone and vinyl acetate and poloxamer; and said pharmaceutically acceptable excipient is sodium lauryl sulfate, and a) said Ivacaftor complex is characterized by infrared (ATR) spectrum having characteristic absorption peaks at 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$; and b) said Ivacaftor complex has characteristic Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$.

In some embodiments, said compositions may additionally include one or more pharmaceutically acceptable excipients, auxiliary materials, carriers, active agents or combinations thereof.

In an embodiment, said Ivacaftor complex has a particle size between 10 nm and 600 nm.

In an embodiment said Ivacaftor complex has a particle size in the range between 10 nm and 400 nm.

In an embodiment, said Ivacaftor complex is instantaneously redispersible in physiological relevant media.

In an embodiment, said Ivacaftor complex has increased dissolution rate compared to the commercially available form of Ivacaftor, both alone and in combination (KALYDECO® and ORKAMBI®).

In an embodiment, said Ivacaftor complex is stable in solid form and in colloid solution and/or dispersion.

In an embodiment, said Ivacaftor complex has apparent solubility in water is at least 1 mg/mL.

In an embodiment, said Ivacaftor complex exhibits X-ray amorphous character in the solid form.

In an embodiment, said Ivacaftor complex has a PAMPA permeability of at least $0.2*10^{-6}$ cm/s when dispersed in distilled water, which does not decrease in time for at least 6 months.

In an embodiment, the variability of exposure of the Ivacaftor complex is significantly reduced compared to the commercially available form, both alone and in combination (KALYDECO® and ORKAMBI®).

In an embodiment, said Ivacaftor complex has no observable food effect, which allows the opportunity of precise dosing and ease of administration of the reconstituted complex in solution form.

In an embodiment said Ivacaftor complex comprises a copolymer of vinylpyrrolidone and vinylacetate and poloxamer and sodium lauryl sulfate, or its pharmaceutical composition characterized by the Raman spectrum shown in FIG. 8 and ATR spectrum shown in FIG. 9.

In an embodiment, said Ivacaftor complex is characterized by characteristic Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 $cm^{-1}$, 1295 $cm^{-1}$, 1361 $cm^{-1}$, 1450 $cm^{-1}$, 1528 $cm^{-1}$, 1573 $cm^{-1}$, 1618 $cm^{-1}$, 1677 $cm^{-1}$, 1738 $cm^{-1}$, 746 $cm^{-1}$, 2884 $cm^{-1}$ and 2936 $cm^{-1}$.

In an embodiment, said Ivacaftor complex is characterized by characteristic Raman shifts at 1082 $cm^{-1}$, 1233 $cm^{-1}$, 1284 $cm^{-1}$, 1361 $cm^{-1}$, 1528 $cm^{-1}$, 1618 $cm^{-1}$ and 1738 $cm^{-1}$.

In an embodiment, said Ivacaftor complex is characterized by ATR spectrum having characteristic peaks at 588 $cm^{-1}$, 628 $cm^{-1}$, 767 $cm^{-1}$, 842 $cm^{-1}$, 962 $cm^{-1}$, 1019 $cm^{-1}$, 1108 $cm^{-1}$, 1148 $cm^{-1}$, 1240 $cm^{-1}$, 1343 $cm^{-1}$, 1370 $cm^{-1}$, 1425 $cm^{-1}$, 1465 $cm^{-1}$, 1525 $cm^{-1}$, 1567 $cm^{-1}$, 1666 $cm^{-1}$ and 1732 $cm^{-1}$.

In an embodiment, said Ivacaftor complex is characterized by ATR spectrum having characteristic peaks at 628 $cm^{-1}$, 767 $cm^{-1}$, 1108 $cm^{-1}$, 1370 $cm^{-1}$, 1465 $cm^{-1}$ and 1666 $cm^{-1}$.

In an embodiment said Ivacaftor complex comprises
  a) Ivacaftor; or a combination of active compounds including Ivacaftor;
  b) a complexing agent which is chosen from the group consisting of a copolymer of vinylpyrrolidone and vinylacetate and a poloxamer, or combinations thereof; and
  c) sodium lauryl sulfate as a pharmaceutically acceptable excipient.

In an embodiment, said Ivacaftor complex comprises a complexation agent which is chosen from the group consisting of a copolymer of vinylpyrrolidone and vinylacetate, and a poloxamer which is poloxamer 407 or poloxamer 338, or combinations thereof; and a pharmaceutically acceptable excipient which is sodium lauryl sulfate, in a total amount comprising from about 1.0 weight % to about 95.0 weight % based on the total weight of the complex.

In an embodiment, said Ivacaftor complex comprises a complexation agent which is chosen from the group consisting of a copolymer of vinylpyrrolidone and vinylacetate, and a poloxamer which is poloxamer 407 or poloxamer 338, or combinations thereof; and a pharmaceutically acceptable excipient which is sodium lauryl sulfate, in a total amount comprising from about 50 weight % to about 95 weight % of the total weight of the complex.

The stable complex of Ivacaftor comprises
a. 5-40% by weight of Ivacaftor, or a salt or derivative thereof;
b. 20-80% by weight of a copolymer of vinylpyrrolidone and vinylacetate;
c. 5-40% by weight of sodium lauryl sulfate; and optionally
d. 0-50% by weight of a poloxamer.

The manufacturing of the stable complex of Ivacaftor comprises the step of mixing a pharmaceutically acceptable solution containing Ivacaftor and at least one complexing agent and optionally one or more pharmaceutically acceptable excipients with an aqueous solution containing optionally least one pharmaceutically acceptable excipient.

In an embodiment said Ivacaftor complex is obtained via a mixing process.

In an embodiment said Ivacaftor complex is obtained via a continuous flow mixing process.

In an embodiment said process is performed in a continuous flow instrument.

In an embodiment said continuous flow instrument is a microfluidic flow instrument.

In an embodiment, said Ivacaftor complex is not obtained via a milling process, high pressure homogenization process, encapsulation process and solid dispersion processes.

In an embodiment, the solvent of said pharmaceutically acceptable solution is chosen from water, methanol, ethanol, 1-propanol, 2-propanol, acetone, acetonitrile, dimethyl-sulfoxide, tetrahydrofuran, methyl-ethyl ketone, or combinations thereof.

In an embodiment, said pharmaceutically acceptable solvent is tetrahydrofuran.

In an embodiment, said pharmaceutically acceptable solvent and said aqueous solution are miscible with each other.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 35 to 45% weight of the final solution.

In an embodiment, said aqueous solution comprises 25 to 35% weight of the final solution.

In an embodiment, said aqueous solution comprises 15 to 25% weight of the final solution.

In an embodiment, said aqueous solution comprises 5 to 15% weight of the final solution.

Disclosed herein is a pharmaceutical composition comprising the Ivacaftor complex together with pharmaceutically acceptable carrier.

The complex Lumacaftor formulation comprises Lumacaftor; a complexing agent which is a copolymer of vinylpyrrolidone and vinylacetate and sodium lauryl sulfate as a pharmaceutically acceptable excipient; said complexes characterized in that they possess at least one of the following properties:
a) is instantaneously redispersable in physiological relevant media;
b) is stable in solid form and in colloid solution and/or dispersion;
c) has apparent solubility in water of at least 1 mg/mL;
d) has a PAMPA permeability of at least $2*10^{-6}$ cm/s when dispersed in FaSSIF or FeSSIF biorelevant media, which does not decrease in time at least for 6 month;
e) exhibits no observable food effect in-vitro.

In an embodiment, said Lumacaftor complex possesses at least two of the properties described in a)–e).

In an embodiment, said Lumacaftor complex possesses at least three of the properties described in a)–e).

Lumacaftor complex formulations possess instantaneous redispersibility, increased apparent solubility and permeability in fasted and fed state simulation that is expected to deliver full absorption and the elimination of the food effect which deliver the opportunity of precise dosing and ease of administration of the reconstituted complex in solution form.

The expression Lumacaftor is generally used for Lumacaftor, or its salts or its derivatives.

In an embodiment, said complexation agent used in the Lumacaftor complex is a copolymer of vinylpyrrolidone and vinylacetate.

In an embodiment, said copolymer of vinylpyrrolidone and vinyl acetate has a 60:40 ratio of vinylpyrrolidone:vinyl acetate monomers.

In an embodiment, said pharmaceutically acceptable excipient used in the Lumacaftor complex is sodium lauryl sulfate.

In an embodiment, said Lumacaftor complex formulation is characterized by
a) Raman shifts at 553 $cm^{-1}$, 602 $cm^{-1}$, 635 $cm^{-1}$, 654 $cm^{-1}$, 747 $cm^{-1}$, 841 $cm^{-1}$, 899 $cm^{-1}$, 934 $cm^{-1}$, 1002 $cm^{-1}$, 1021 $cm^{-1}$, 1117 $cm^{-1}$, 1205 $cm^{-1}$, 1232 $cm^{-1}$, 1310 $cm^{-1}$, 1352 $cm^{-1}$, 1372 $cm^{-1}$, 1428 $cm^{-1}$, 1444 $cm^{-1}$, 1497 $cm^{-1}$, 1592 $cm^{-1}$, 1609 $cm^{-1}$, 1677 $cm^{-1}$ and 1737 $cm^{-1}$; and
b) infrared (ATR) peaks at 635 $cm^{-1}$, 703 $cm^{-1}$, 747 $cm^{-1}$, 837 $cm^{-1}$, 1021 $cm^{-1}$, 1165 $cm^{-1}$, 1231 $cm^{-1}$, 1288 $cm^{-1}$, 1369 $cm^{-1}$, 1423 $cm^{-1}$, 1462 $cm^{-1}$, 1494 $cm^{-1}$, 1667 $cm^{-1}$ and 1731 $cm^{-1}$.

In some embodiments, the pharmaceutical compositions may additionally include one or more pharmaceutically acceptable excipients, auxiliary materials, carriers, active agents or combinations thereof.

In an embodiment, said Lumacaftor complexes have a particle size between 10 nm and 500 nm.

In an embodiment, said particle size is between 10 nm and 250 nm.

In an embodiment, said Lumacaftor complex has increased dissolution rate compared to the commercially available form of Lumacaftor (crystalline form of Lumacaftor).

In an embodiment, said Lumacaftor complex is stable in solid form and in colloid solution and/or dispersion.

In an embodiment, said Lumacaftor complex has an apparent solubility in water is at least 1 mg/mL.

In an embodiment, said Lumacaftor complex exhibits X-ray amorphous character in the solid form.

In an embodiment, said Lumacaftor complex has a PAMPA permeability of at least $2*10^{-6}$ cm/s when dispersed in distilled water, which does not decrease in time at least for 6 months.

In an embodiment, the variability of exposure of said Lumacaftor complex is significantly reduced compared to the commercially available form (ORKAMBI®).

In an embodiment, said Lumacaftor complex has no observable food effect in-vitro, which allows the opportunity of precise dosing and ease of administration of the reconstituted complex in solution form.

In an embodiment said Lumacaftor complex or its pharmaceutical composition characterized by Raman spectrum shown in FIG. 10 and ATR spectrum shown in FIG. 11.

In an embodiment said Lumacaftor complex is characterized by Raman shifts at 553 $cm^{-1}$, 602 $cm^{-1}$, 635 $cm^{-1}$, 654 $cm^{-1}$, 747 $cm^{-1}$, 841 $cm^{-1}$, 899 $cm^{-1}$, 934 $cm^{-1}$, 1002 $cm^{-1}$, 1021 $cm^{-1}$, 1117 $cm^{-1}$, 1205 $cm^{-1}$, 1232 $cm^{-1}$, 1310 $cm^{-1}$, 1352 $cm^{-1}$, 1372 $cm^{-1}$, 1428 $cm^{-1}$, 1444 $cm^{-1}$, 1497 $cm^{-1}$, 1592 $cm^{-1}$, 1609 $cm^{-1}$, 1677 $cm^{-1}$ and 1737 $cm^{-1}$.

In an embodiment said Lumacaftor complex is characterized by infrared (ATR) peaks at 635 cm$^{-1}$, 703 cm$^{-1}$, 747 cm$^{-1}$, 837 cm$^{-1}$, 1021 cm$^{-1}$, 1165 cm$^{-1}$, 1231 cm$^{-1}$, 1288 cm$^{-1}$, 1369 cm$^{-1}$, 1423 cm$^{-1}$, 1462 cm$^{-1}$, 1494 cm$^{-1}$, 1667 cm$^{-1}$ and 1731 cm$^{-1}$.

In an embodiment said Lumacaftor complex comprises
a) Lumacaftor; or a combination of active compounds including Lumacaftor;
b) a complexing agent which is a copolymer of vinylpyrrolidone and vinylacetate; and
c) sodium lauryl sulfate as an excipient.

In an embodiment, said complex Lumacaftor formulation comprises a complexation agent which is a copolymer of vinylpyrrolidone and vinylacetate and a pharmaceutically acceptable excipient which is sodium lauryl sulfate, in a total amount ranging from about 1.0 weight % to about 95.0 weight % based on the total weight of the complex.

In an embodiment, said Lumacaftor complex comprises complexation agent which is a copolymer of vinylpyrrolidone and vinylacetate and pharmaceutically acceptable excipient which is sodium lauryl sulfate comprise 50 weight % to about 95 weight % of the total weight of the complex.

The stable complex of Lumacaftor comprises
a. 5-40% by weight of Lumacaftor, or a salt or derivatives thereof;
b. 50-90% by weight of a copolymer of vinylpyrrolidone and vinylacetate;
c. 0.01-40% by weight of sodium lauryl sulfate The manufacturing of the stable complex of Lumacaftor comprises the step of mixing a pharmaceutically acceptable solution containing Lumacaftor and at least one complexing agent and optionally one or more pharmaceutically acceptable excipient with an aqueous solution containing optionally at least one pharmaceutically acceptable excipient.

In an embodiment said Lumacaftor complex is obtained via a mixing process.

In an embodiment said Lumacaftor complex is obtained via a continuous flow mixing process.

In an embodiment said process is performed in a continuous flow instrument.

In an embodiment said continuous flow instrument is a microfluidic flow instrument.

In an embodiment, said Lumacaftor complex is not obtained via a milling process, high pressure homogenization process, encapsulation process and solid dispersion processes.

In an embodiment, the solvent of said pharmaceutically acceptable solution is chosen from methanol, ethanol, 1-propanol, 2-propanol, acetone, acetonitrile, dimethyl-sulfoxide, tetrahydrofuran, methyl-ethyl ketone or combinations thereof.

In an embodiment, said pharmaceutically acceptable solvent is methanol.

In an embodiment, said pharmaceutically acceptable solvent and said aqueous solution are miscible with each other.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 35 to 45% weight of the final solution.

In an embodiment, said aqueous solution comprises 25 to 35% weight of the final solution.

In an embodiment, said aqueous solution comprises 15 to 25% weight of the final solution.

In an embodiment, said aqueous solution comprises 5 to 15% weight of the final solution.

Disclosed herein is a pharmaceutical composition comprising the complex together with pharmaceutically acceptable carriers.

In an embodiment, the complexing agents themselves or together with the pharmaceutically acceptable excipients have the function to form a complex structure with an active pharmaceutical ingredient through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions. The complexing agents, pharmaceutically accepted excipients and active ingredients are selected from the group of complexing agents, pharmaceutically accepted excipients and active ingredients which are able to form such complex structures through non-covalent secondary interactions.

The pharmaceutical combination composition comprises
a) Complex Ivacaftor formulation comprising Ivacaftor, a complexing agent which is a copolymer of vinylpyrrolidone and vinylacetate and sodium lauryl sulfate as a pharmaceutically acceptable excipient; and
b) Complex Lumacaftor formulation comprising Lumacaftor, a complexing agent which is a copolymer of vinylpyrrolidone and vinylacetate and sodium lauryl sulfate as a pharmaceutically acceptable excipient; and
c) optionally, additional pharmaceutically acceptable excipients wherein said pharmaceutical combination composition characterized in that they possess at least one of the following properties:
a) is instantaneously redispersable in physiological relevant media;
b) is stable in solid form and in colloid solution and/or dispersion;
c) apparent solubility both for Ivacaftor and Lumacaftor in water is at least 1 mg/mL;
d) PAMPA permeability both for Ivacaftor and Lumacaftor complex formulations is at least 0.2*10$^{-6}$ cm/s for Ivacaftor and 2*10$^{-6}$ cm/s for Lumacaftor when dispersed in FaSSIF or FeSSIF biorelevant media, which does not decrease in time at least for 6 month;
e) exhibits no observable food effect in-vitro.

In an embodiment, said pharmaceutical combination composition possesses at least two of the properties described in a)-e).

In an embodiment, said pharmaceutical combination composition possesses at least three of the properties described in a)-e).

In an embodiment, said pharmaceutical combination composition possesses instantaneous redispersibility, increased apparent solubility and permeability in fasted and fed state simulation that is expected to deliver full absorption and the elimination of the food effect which deliver the opportunity of precise dosing and ease of administration of the reconstituted pharmaceutical combination composition in solution form.

In some embodiments, said pharmaceutical combination composition may additionally include one or more pharmaceutically acceptable excipients, auxiliary materials, carriers, active agents or combinations thereof.

In an embodiment, said pharmaceutical combination composition has increased dissolution rate compared to the commercially available form (ORKAMBI®).

In an embodiment, said pharmaceutical combination composition is stable in solid form and in colloid solution and/or dispersion.

In an embodiment, said pharmaceutical combination composition has PAMPA permeability that is at least $0.2*10^{-6}$ cm/s for Ivacaftor and $2*10^{-6}$ cm/s for Lumacaftor when dispersed in water or biorelevant media, which does not decrease in time at least for 6 months.

In an embodiment, the variability of exposure of said pharmaceutical combination composition is significantly reduced compared to the commercially available form (ORKAMBI®).

In an embodiment, said pharmaceutical combination composition has no observable food effect in-vitro, which allows the opportunity of precise dosing and ease of administration of the reconstituted pharmaceutical combination composition in solution form.

In an embodiment, said pharmaceutical combination composition comprises complexation agent which is chosen from the group consisting of a copolymer of vinylpyrrolidone and vinylacetate, and a poloxamer, or combinations thereof, and a pharmaceutically acceptable excipient which is sodium lauryl sulfate, in a total amount ranging from about 1.0 weight % to about 95.0 weight % based on the total weight of the pharmaceutical combination composition.

In an embodiment, said pharmaceutical combination composition comprises complexation agent which is chosen from the group consisting of a copolymer of vinylpyrrolidone and vinylacetate, and a poloxamer, or combinations thereof, and a pharmaceutically acceptable excipient which is sodium lauryl sulfate, in a total amount ranging from about 50 weight % to about 95 weight % of the total weight of the pharmaceutical combination composition.

In an embodiment, said pharmaceutical combination composition comprises of 50 to 300 mg Ivacaftor equivalent complex Ivacaftor formulation in combination with 25 to 250 mg Lumacaftor equivalent complex Lumacaftor formulation.

In an embodiment, the manufacturing of the pharmaceutical combination composition includes the steps of:
1) mixing a pharmaceutically acceptable solution containing Ivacaftor and at least one complexing agent and optionally one or more pharmaceutically acceptable excipients with an aqueous solution containing optionally least one pharmaceutically acceptable excipient and solidification of the resulted solution mixture;
2) mixing a pharmaceutically acceptable solution containing Lumacaftor and at least one complexing agent and optionally one or more pharmaceutically acceptable excipients with an aqueous solution containing optionally least one pharmaceutically acceptable excipient and solidification of the resulted solution mixture; and
3) the step of blending and granulation of the solidified Ivacaftor and Lumacaftor complex formulations.

Alternatively, the solutions containing Ivacaftor and Lumacaftor from steps 1) and 2) can be combined into a single step using a solution mixture containing the complex Ivacaftor and Lumacaftor, followed by step 3).

In an embodiment said Ivacaftor complex is obtained via a mixing process.

In an embodiment said Lumacaftor complex is obtained via a mixing process.

In an embodiment said complex of Ivacaftor and Lumacaftor is obtained via a mixing process.

In an embodiment said mixing process is a continuous flow mixing process.

In an embodiment said process is performed in a continuous flow instrument.

In an embodiment said continuous flow instrument is a microfluidic flow instrument.

In an embodiment, the solvent of said pharmaceutically acceptable solution is chosen from methanol, ethanol, 1-propanol, 2-propanol, acetone, acetonitrile, dimethyl-sulfoxide, tetrahydrofuran, methyl-ethyl ketone or combinations thereof.

In an embodiment, said pharmaceutically acceptable solvent is a combination of methanol and tetrahydrofuran.

In an embodiment, said pharmaceutically acceptable solvent and said aqueous solution are miscible with each other.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 35 to 45% weight of the final solution.

In an embodiment, said aqueous solution comprises 25 to 35% weight of the final solution.

In an embodiment, said aqueous solution comprises 15 to 25% weight of the final solution.

In an embodiment, said aqueous solution comprises 5 to 15% weight of the final solution.

In an embodiment, a pharmaceutical composition comprising the complex together with pharmaceutically acceptable carriers.

The pharmaceutical combination composition of the invention comprising complex Ivacaftor and complex Lumacaftor formulations can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The pharmaceutical combination compositions can be formulated by adding different types of pharmaceutically acceptable excipients for oral administration in solid, liquid, local (powders, ointments or drops), or topical administration, and the like.

In an embodiment, the dosage form of the invention is a solid dosage form, although any pharmaceutically acceptable dosage form can be utilized.

Solid dosage forms for oral administration include, but are not limited to, capsules, tablets, pills, powders (sachet), and granules. In such solid dosage forms, the complex formulations is admixed with at least one of the following: one or more inert excipients (or carriers): (a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide; (b) sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid; (c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain complex silicates and sodium carbonate; (e) solution retarders, such as acrylates, cellulose derivatives, paraffin; (f) absorption accelerators, such as quaternary ammonium compounds; (g) wetting agents, such as polysorbates, cetyl alcohol and glycerol monostearate; (h) lubricants such as talc, stearic acid and its derivatives, solid polyethylene glycols, sodium lauryl sulfate, glyceryl behenate, medium-chain triglycerides or mixtures thereof. For capsules, tablets, and pills, the dosage forms may also comprise buffering agents.

In an embodiment, the dosage form of the invention is liquid dispersible granules in a sachet form.

In an embodiment, said liquid dispersible granules comprise said complex Ivacaftor formulation and said complex Lumacaftor formulation and optionally pharmaceutically acceptable excipients.

In an embodiment, said pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, and magnesium oxide.

In an embodiment, pharmaceutically acceptable excipients selected from the group of sweetening, flavoring, aromatizing and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, and tartaric acid.

Further disclosed herein is liquid dispersible granules comprising
a. 25-95% pharmaceutical combination composition comprising complex Ivacaftor and complex Lumacaftor formulations;
b. 5-75% fillers or extenders;
c. 0.5-25% binders;
d. 0.1-5% sweetening, flavoring, aromatizing and perfuming agents;
wherein said liquid dispersible granules disperses within 3 min in liquid; and wherein said liquid dispersible granules are obtained by wet or dry processes.

In an embodiment, said dispersion time is between 0.1 min and 10 min.

In an embodiment, said dispersion time is between 0.1 min and 5 min.

In an embodiment, said dispersion time is between 0.1 min and 3 min.

In an embodiment, said dispersion time is between 0.1 min and 1 min.

In an embodiment, said dispersion time is between 0.1 min and 1 min.

In an embodiment, Hausner-ratio of the said liquid dispersible granules is less than 1.25 more preferably 1.00-1.18

In an embodiment, Hausner-ratio of the said liquid dispersible granules is between 1.00 and 1.18.

In an embodiment, the particle size (D(90)) of said liquid dispersible granules is less than 2000 micrometers.

In an embodiment, 60-99% of the said liquid dispersible granules are in the size range of 160-1200 micrometers In an embodiment, said liquid is water, saliva, other physiologically or biologically acceptable fluid.

Advantages of the pharmaceutical combination composition of the invention include, but are not limited to (1) physical and chemical stability, (2) instantaneous redispersibility, (3) stability in colloid solution or dispersion in the therapeutic time window, (4) increased apparent solubility and permeability compared to the conventional formulations, (5) no observable food effect which deliver the opportunity of precise dosing and ease of administration of the reconstituted complex formulation in solution form, (6) good processability.

Beneficial features are as follows: the good/instantaneous redispersibility of the pharmaceutical composition in water, biologically relevant media, e.g.; physiological saline solution, pH=2.5 HCl solution, FessiF and FassiF media and gastro intestinal fluids and adequate stability in colloid solutions and/or dispersion in the therapeutic time window.

In an embodiment, the pharmaceutical combination composition has increased apparent solubility and permeability. In some embodiments, the apparent solubility and permeability of the pharmaceutical combination composition is at least 1 mg/mL and $0.2 \times 10^{-6}$ cm/s, respectively.

The pharmaceutical combination composition possesses instantaneous redispersibility, increased apparent solubility and permeability, no observable food effect which deliver the opportunity of precise dosing and ease of administration of the redispersed solid.

BRIEF DESCRIPTION OF THE DRAWINGS

The accompanying figures, which are incorporated and form part of the specification, merely illustrate certain embodiments and should not be construed as limiting. They are meant to serve to explain specific modes to those skilled in the art.

FIG. 1. shows physical appearance and stability of the produced complex Ivacaftor formula during the flow optimization.

FIG. 2. shows apparent solubility of complex Ivacaftor and Lumacaftor formulations alone and in combinations.

FIG. 4. Ivacaftor and Lumacaftor dissolution from the pharmaceutical combination composition prepared by spray drying in combination and powder blending.

FIG. 8. shows PAMPA permeability of complex Ivacaftor and complex Lumacaftor formulations stored at different conditions.

FIG. 9. shows PAMPA permeability of complex Ivacaftor and complex Lumacaftor formulations in the pharmaceutical composition stored at different conditions.

FIG. 17. shows comparative apparent solubility data of different Ivacaftor formulations.

FIG. 19. shows particle size of different of Ivacaftor and Lumacaftor formulation.

FIG. 20. shows apparent solubility of Lumacaftor formulations.

FIG. 21. shows comparative PAMPA permeability of Lumacaftor formulations.

FIG. 24. shows comparative PAMPA permeability of different, Orkambi equivalent Ivacaftor and Lumacaftor formulations.

FIG. 26. shows pharmacokinteic parameters following the oral administration of novel complex in the fasted and in the fed state to beagle dogs at 3 mg/kg dose (N=4).

EXAMPLES

Figure 3:
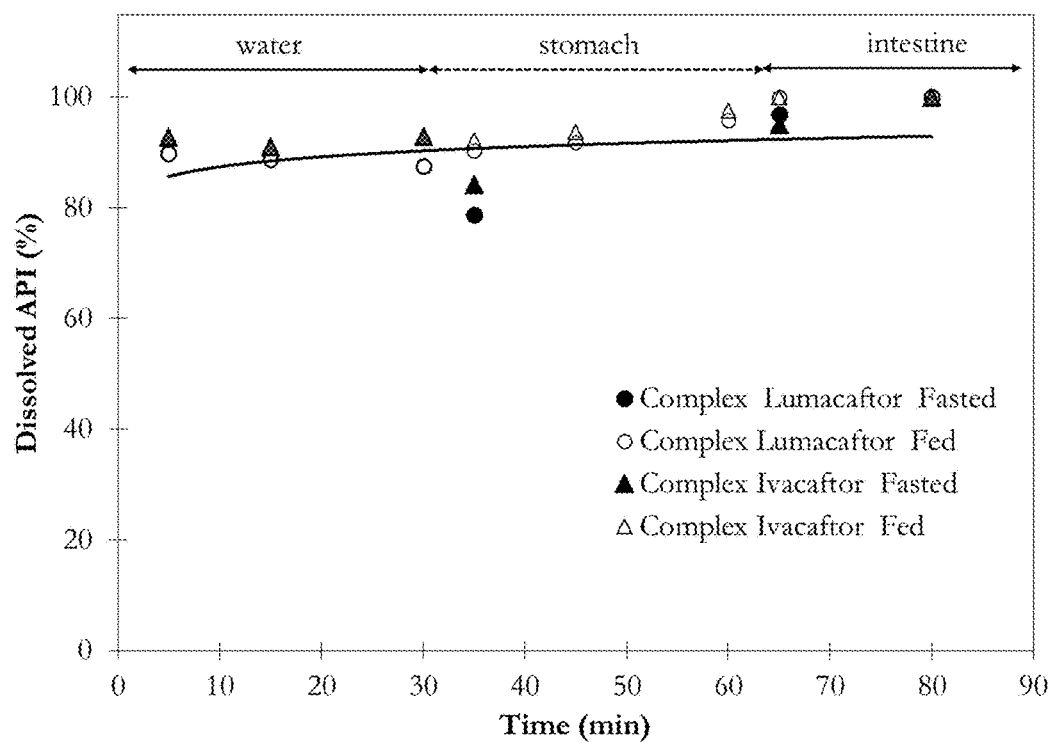
FIG. 3. shows GI tract simulated dissolution of Ivacaftor and Lumacaftor from the pharmaceutical composition disclosed herein.

Specific embodiments will further be demonstrated by the following examples. It should be understood that these examples are disclosed only by way of illustration and should not be construed as limiting the scope.

Manufacturing of Complex Ivacaftor Formulation

A solution mixture of complex Ivacaftor formulation was prepared by mixing process. Solution 1 containing 500 mg Ivacaftor and 1500 mg vinylpyrrolidone and vinylacetate copolymer (Luviskol VA 64) and 1000 mg poloxamer (Poloxamer 338-Pluronic F108) in 100 mL tetrahydrofuran was mixed with aqueous Solution 2 containing 500 mg sodium lauryl sulfate in 100 mL ultrapurified water in different flow rates. 1:1 Solvent 1:Solvent 2 ratio was used. The colloid solution of the complex Ivacaftor formulation was produced at atmospheric pressure and 20-50° C. temperature. The appearance and stability of the produced colloid solution were monitored. Based on the physical appearance and stability of the produced complex Ivacaftor formulation in colloid solution, the best composition was selected for spray-drying experiments. FIG. 1 summarizes the results.

The solidification of the colloid solution was performed by spray-drying technique. 5 mg/mL Ivacaftor, 15 mg/mL vinylpyrrolidone and vinylacetate copolymer (Luviskol VA 64) and 10 mg/mL poloxamer (Poloxamer 338-Pluronic F108) in tetrahydrofuran and 5 mg/mL sodium lauryl sulfate in water were chosen for starting concentrations. The ratio of the solutions was found to be optimal at 1:1 ratio. The colloid solution of the complex Ivacaftor formulation prepared by the optimal parameter sets was spray-dried (Yamato DL-410/GAS410) in order to obtain solid powder. The spray-drying process was optimized. The optimal production parameters were found to be $T_{inlet}$=95° C., $V_{air}$=0.8 m³/min, $M_{in}$=18 mL/min, p=1 bar, $T_{out}$=58-59° C.

Manufacturing of Complex Lumacaftor Formulation

A solution mixture of Lumacaftor complex formulation was prepared by continuous flow mixing approach. 20 mL Solution 1 was prepared by dissolving 40 mg Lumacaftor and 180 mg copolymer of vinylpyrrolidone and vinylacetate in 20 mL methanol. The prepared Solution 1 was mixed with Solution 2 containing 24 mg sodium lauryl sulfate in 80 mL water at 1:4 volume ratio in order to produce complex Lumacaftor formulation. The solution mixture of the complex Lumacaftor formulation was produced at atmospheric pressure and ambient temperature. The produced solution mixture was frozen on dry-ice and then it was lyophilized using a freeze drier equipped with −110° C. ice condenser, with a vacuum pump. Spray-drying was also applicable to produce solid powder from the solution mixture of complex Lumacaftor formulation.

Manufacturing of Pharmaceutical Combination Composition

Pharmaceutical composition was prepared by blending the powders of complex Ivacaftor and Lumacaftor formulations. The resulted pharmaceutical composition contained the complex Ivacaftor and complex Lumacaftor formulation in 125:200 active compound equivalent ratio.

A solution mixture of pharmaceutical combination composition was prepared by mixing process. Solution 1 containing 192 mg Ivacaftor and 308 mg Lumacaftor and 1000 mg vinylpyrrolidone and vinylacetate copolymer (Luviskol VA 64) in 100 mL solvent mixture of methanol and tetrahydrofuran having volume ratio of 5:2 was mixed with aqueous Solution 2 containing 150 mg sodium lauryl sulfate in 400 mL ultrapurified water in different flow rates. Solvent 1:Solvent 2 ratio was 1:4. The colloid solution of the complex Ivacaftor formulation was produced at atmospheric pressure and 25° C. temperature. The solidification of the colloid solution was performed by spray-drying technique.

1.92 mg/mL Ivacaftor, 3.08 mg/mL Lumacaftor and 10 mg/mL vinylpyrrolidone and vinylacetate copolymer (Luviskol VA 64) in methanol:tetrahydrofuran solvent mixture at volume ratio of 5:2 and 0.375 mg/mL sodium lauryl sulfate in water were chosen for starting concentrations. The ratio of the Solution 1 and Solution 2 was found to be optimal at 1:4 ratio. The prepared solution mixture was spray-dried (Yamato DL-410/GAS410) in order to obtain solid powder. The optimal spray-drying parameters were found to be $T_{inlet}$=90° C., $V_{air}$=0.85 m³/min, $M_{in}$=20 mL/min, atomizing pressure=1 bar, $T_{out}$=50° C.

Preparation of Liquid Dispersible Granules of Complex Ivacaftor Formulation

Liquid dispersible granules comprising the complex Ivacaftor formulations can be obtained by wet or dry granulation processes.

Dry granulation process includes, but not limited to the slugging or roll compaction of the powder formulation of complex Ivacaftor into compacts and breaking of the compacts into granules with appropriate mesh size. The obtained granules can be mixed with excipients chosen from the group consisting of fillers, extenders, binders, disintegrating agents, wetting agents, lubricants, taste masking, sweetening, flavoring, and perfuming agents.

Dry granulation technique can be also applied on the powder blend of complex Ivacaftor formulations. Powder blend consists of the powder formulation of complex Ivacaftor and excipients chosen from the group consisting of fillers, extenders, binders, disintegrating agents, wetting agents, lubricants, taste masking, sweetening, flavoring, and perfuming agents and prepared by mixing of powders. Slugging or roll compaction are used to manufacture compacts from the powder blend. Then the compacts are broken into granules with appropriate mesh size.

Wet granulation process covers the moisturizing of the powder formulations of complex Ivacaftor (direct granulation) or moisturizing the excipients chosen from the group consisting of fillers, extenders, binders, disintegrating agents, wetting agents, lubricants, taste masking, sweetening, flavoring, and perfuming agents with aqueous solution of pharmaceutically acceptable binders and mixing it with the powder formulations of complex Ivacaftor (indirect granulation). The particle size of the granules can be controlled by physical impact before and after the drying step.

Liquid dispersible granules of complex Ivacaftor formulation were prepared by compacting appropriate amount of complex Ivacaftor powder blend using 0.5 ton load. The powder blend comprised of the solid formulation of the complex of Ivacaftor and, optionally, sweetening, flavouring, aromatizing, and perfuming agents. The height of the compact was found to be optimal between 0.8-1.0 mm. The compacts were broken up by physical impact to form granulates. The particle size of the granules was controlled by sieving with appropriate mesh size to achieve 160-800 micrometers particle size.

Preparation of Liquid Dispersible Granules of Complex Lumacaftor Formulation

Liquid dispersible granules comprising the complex Lumacaftor formulations can be obtained by wet or dry granulation processes.

Dry granulation process includes, but not limited to the slugging or roll compaction of the powder formulation of complex Lumacaftor into compacts and breaking of the compacts into granules with appropriate mesh size. The obtained granules can be mixed with fillers, extenders, binders, disintegrating agents, wetting agents, lubricants, taste masking, sweetening, flavoring, and perfuming agents.

Dry granulation technique can be also applied on the powder blend of complex Lumacaftor formulations. Powder blend consists of the powder formulation of complex Lumacaftor and fillers, extenders, binders, disintegrating agents, wetting agents, lubricants, taste masking, sweetening, flavoring, and perfuming agents and prepared by mixing of powders. Slugging or roll compaction are used to manufacture compacts from the powder blend. Then the compacts are broken into granules with appropriate mesh size.

Wet granulation process covers the moisturizing of the powder formulations of complex Lumacaftor (direct granulation) or moisturizing the fillers, extenders, binders, disintegrating agents, wetting agents, lubricants, taste masking, sweetening, flavoring, and perfuming agents with aqueous solution of pharmaceutically acceptable binders and mixing it with the powder formulations of complex Lumacaftor (indirect granulation). The particle size of the granules can be controlled by physical impact before and after the drying step.

Liquid dispersible granules of complex Lumacaftor formulation were prepared by compacting appropriate amount of complex Lumacaftor powder blend using 0.5 ton load. The powder blend comprised of the solid formulation of the complex of Lumacaftor and sweetening, flavoring, aromatizing and perfuming agents. The height of the compact was found to be optimal between 0.8-1.0 mm. The compacts were broken up by physical impact to form granulates. The particle size of the granules was controlled by sieving with appropriate mesh size to achieve 160-800 micrometers particle size.

Preparation of Liquid Dispersible Granules of Pharmaceutical Combination Composition Liquid dispersible granules of pharmaceutical combination composition can be obtained by blending the liquid dispersible granule or pellets of complex Ivacaftor formulation and complex Lumacaftor formulation; or mixing the complex Ivacaftor formulation with the complex Lumacaftor formulation before granulation, pelletising; or blending the liquid dispersible granules or pellets of the complex Ivacaftor formulation or complex Lumacaftor formulation with the solid form of the complex Ivacaftor formulation or complex Lumacaftor formulation.

Liquid dispersible granules of pharmaceutical combination composition can be obtained by compacting appropriate amount of pharmaceutical combination composition prepared by spray-drying in combination using 0.5-3 ton load. The powder comprised of the solid formulation of the pharmaceutical combination composition and sweetening, flavouring, aromatizing and perfuming agents. The height of the compact was found to be optimal between 0.8-1.0 mm. The compacts were broken up by physical impact to form granulates. The particle size of the granules was controlled by sieving with appropriate mesh size to achieve 160-800 µm particle size.

Blending and mixing include but not limited to container rotating or high shear mixing.

Comparative Solubility Tests

The apparent solubility was measured by UV-VIS spectroscopy or RP-HPLC at room temperature. The samples were dispersed in ultrapurified water in 1-20 mg/mL active ingredient equivalent concentration range. The resulting solutions were filtered by 100 nm disposable syringe filter. The active ingredient content in the filtrate was measured by UV-Vis spectrophotometry or RP-HPLC and the apparent solubility was calculated. The filtrate may contain particles which could not be filtrated out using 100 nm pore size filter. FIG. 2 shows the results.

The apparent solubility of complex Ivacaftor formulation was 0.991; 2.356; 4.924; 9.463 mg/mL and 18.474, when 1; 2.5; 5; 10 and 20 mg/mL Ivacator equivalent formulations were dispersed in ultrapurified water, respectively.

Apparent solubility of complex Ivacaftor formulation was 18.474 mg/mL.

The apparent solubility of complex Lumacaftor formulation was 0.950; 9.839 and 14.913 mg/mL, when 1; 10 and 20 mg/mL Lumacaftor equivalent formulations were dispersed in ultrapurified water, respectively. The apparent solubility of unformulated crystalline Lumacaftor was found to be 0.032 mg/mL.

Solubility of complex Lumacaftor formula was 14.913 mg/mL.

The apparent solubility of pharmaceutical combination composition prepared by powder blending was 1.009; 4.6967; 9.591 mg/mL and 19.9493 mg/mL for Lumacaftor and 0.6117; 2.8444; 5.7553 mg/mL and 11.3187 mg/mL for Ivacaftor, when 1; 5; 10 and 20 mg/mL Lumacaftor equivalent formulations were dispersed in ultrapurified water, respectively.

Apparent solubility of pharmaceutical combination composition prepared by powder blending was 19.9493 mg/mL for Lumacaftor and 11.3187 mg/mL for Ivacaftor.

The apparent solubility of pharmaceutical combination composition prepared by spray drying in combination was 0.9656; 4.8253; 8.9099 mg/mL and 19.2660 mg/mL for Lumacaftor and 0.5969; 3.0105; 5.5397 mg/mL and 12.0467 mg/mL for Ivacaftor, when 1; 5; 10 and 20 mg/mL Lumacaftor equivalent formulations were dispersed in ultrapurified water, respectively.

Apparent solubility of pharmaceutical combination composition prepared by spray drying was 19.2660 mg/mL for Lumacaftor and 12.0467 mg/mL for Ivacaftor.

Dissolution Test

Gastro-intestinal tract simulated drug dissolution tests were performed by dispersing the blended pharmaceutical combination composition described above in purified water. The dispersion contained 1 mg/mL Lumacaftor and 0.625 mg/mL Ivacaftor (identical mixture to ORKAMBI®). After 30 minutes holding time, simulated gastric fluid (SGF V2) was added to dispersion in order to set-up the pH to 1.6 (fasted state simulation) or FeSSIF buffer to increase the pH to 5.8 (fed state simulation). After 60 minutes holding time, the pH of the fasted state simulated dispersion was set-up to pH=6.5 adding maleic acid solution. FaSSIF solution was also added to the dispersion to ensure the fasted condition in the intestine simulation. In case of fed state simulation FeSSIF solution was added to the dispersion.

The dissolved amount of Lumacaftor and Ivacaftor from the blended pharmaceutical combination composition was measured by RP-HPLC after filtration with 0.1 μm pore size filter at different time points. Dissolution of Ivacaftor and Lumacaftor from the blended and granulated complex formulation was instantaneous, within 5 minutes more than 85% of the Ivacaftor and Lumacaftor dissolved from the pharmaceutical composition of present invention both in fasted and fed state simulated condition. (FIG. 3).

Drug dissolution tests were performed by dispersing the pharmaceutical combination composition prepared by powder blending or spray-drying in combination in water. The dissolved amount of Lumacaftor and Ivacaftor was measured by RP-HPLC after filtration with 0.1 μm pore size filter at different time points. Dissolution of Ivacaftor and Lumacaftor prepared by spray drying in combination was instantaneous, within 5 minutes more than 85% of the Ivacaftor and Lumacaftor dissolved from the pharmaceutical composition of present invention in water. (FIG. 4).

Comparative In-vitro PAMPA Assays

PAMPA permeability of the complex formulations was measured and compared to the unformulated crystalline reference active compounds. PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water, FaSSIF and FeSSIF, respectively. The concentration in the receiver compartment was determined by UV-VIS spectrophotometry or RP-HPLC method (Thermo Scientific multiscan GO spectrophotometer or Thermo Surveyor HPLC or Rigol L-3000 series HPLC).

Figure 5:
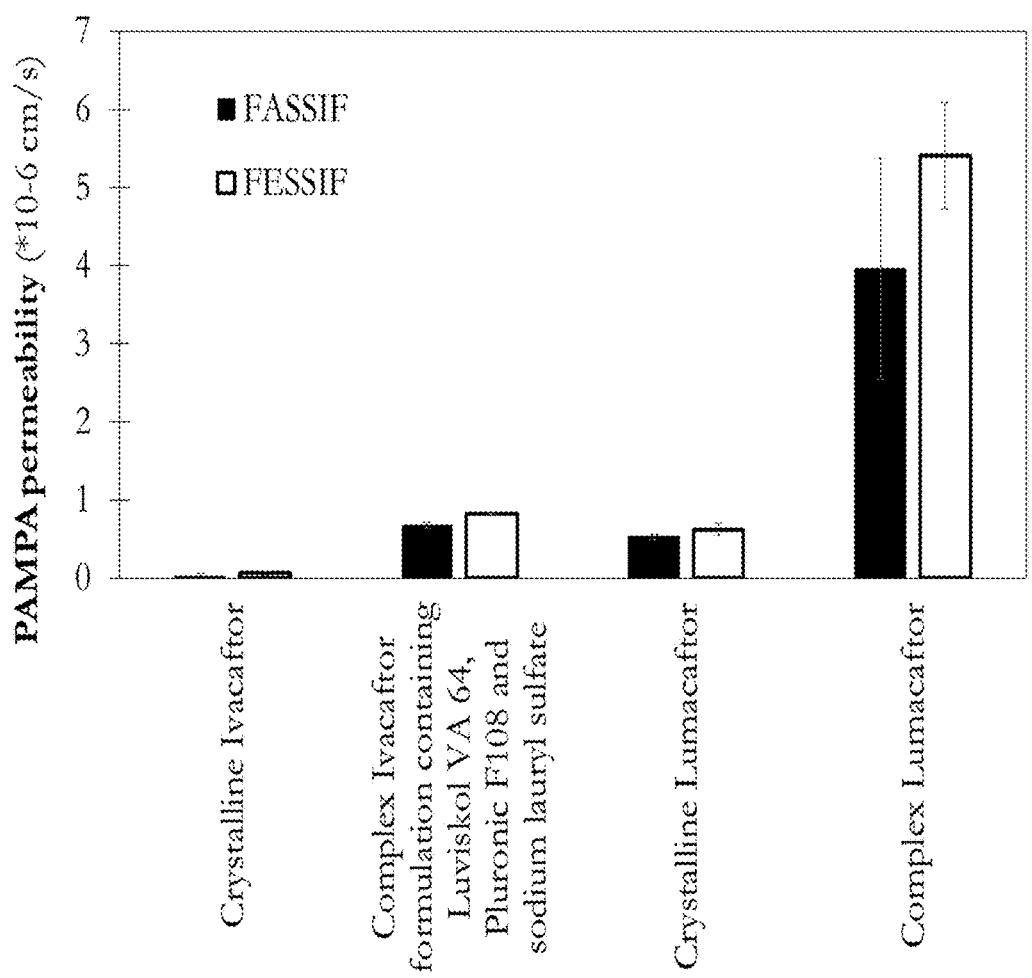
FIG. 5. shows PAMPA permeabilities of complex Ivacaftor formulation and complex Lumacaftor formulation.

PAMPA permeabilities of complex Ivacaftor formulation and complex Lumacaftor formulation were measured in FaSSIF and FeSSIF media and were found to be above $0.5 \times 10^{-6}$ cm/s for Ivacaftor and $2 \times 10^{-6}$ cm/s for Lumacaftor measured by UV-VIS (FIG. 5).

Figure 6:
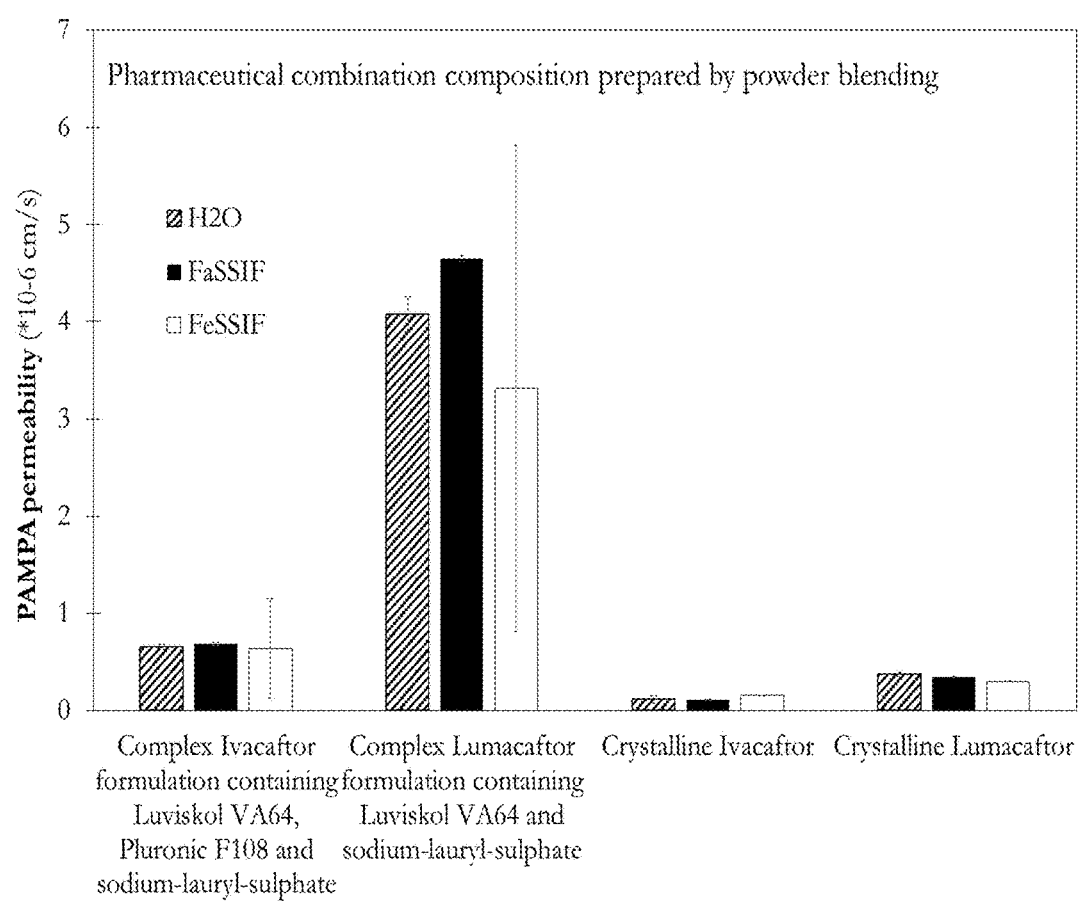
FIG. 6. shows PAMPA permeabilities of complex Ivacaftor formulation and complex Lumacaftor formulation in the pharmaceutical combination composition prepared by powder blending.

PAMPA permeabilities of pharmaceutical combination composition prepared by powder blending was measured in water; FaSSIF and FeSSIF media and were found to be above $0.5 \times 10^{-6}$ cm/s for Ivacaftor and $2 \times 10^{-6}$ cm/s for Lumacaftor measured by UV-VIS (FIG. 6).

Figure 7:
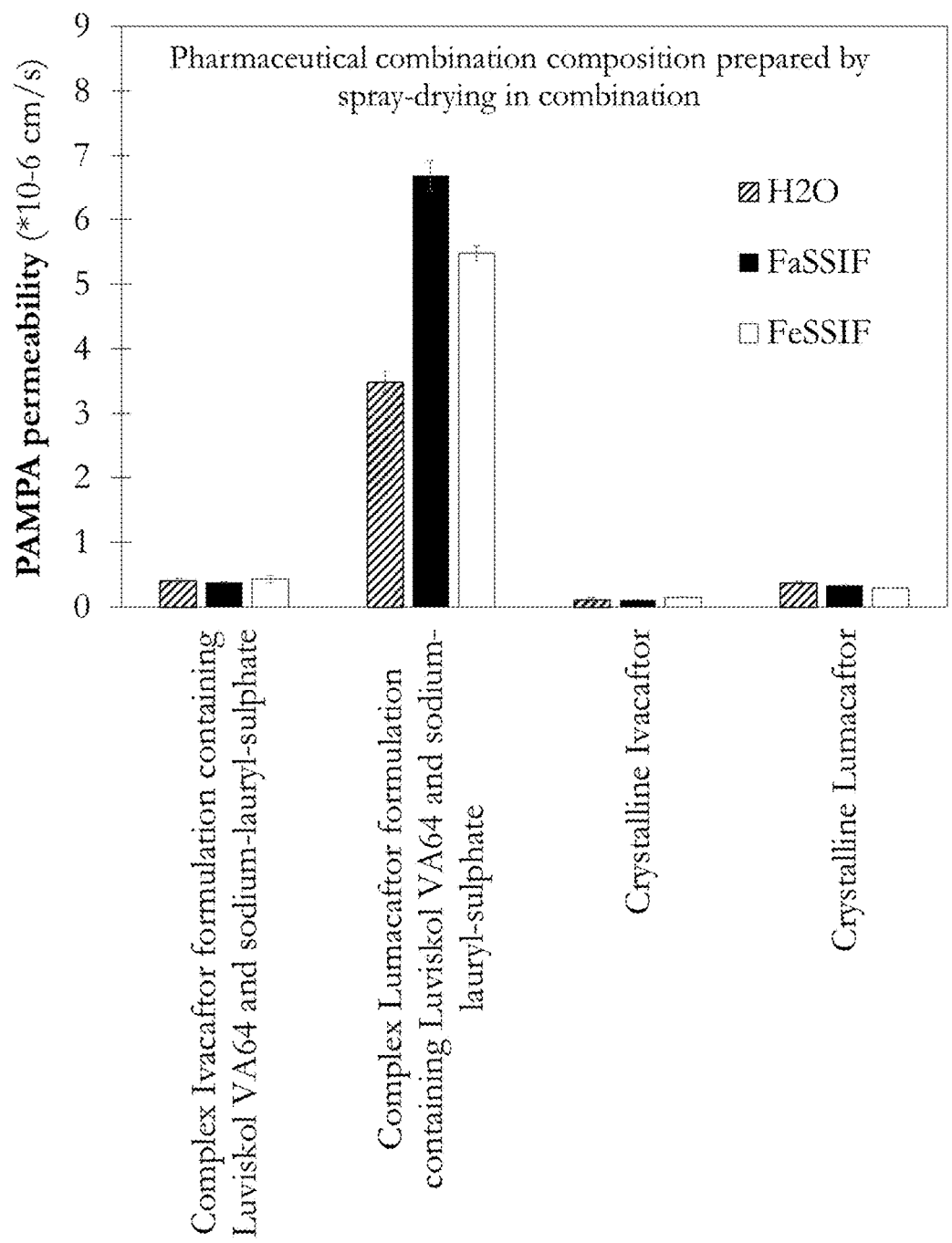
FIG. 7. shows PAMPA permeabilities of complex Ivacaftor formulation and complex Lumacaftor formulation in the pharmaceutical combination composition prepared by spray-drying in combination.

PAMPA permeabilities of pharmaceutical combination composition prepared by spray-drying in combination was measured in water; FaSSIF and FeSSIF media and were found to be above $0.2 \times 10^{-6}$ cm/s for Ivacaftor and $1.5 \times 10^{-6}$ cm/s for Lumacaftor measured by HPLC (FIG. 7).

Stability on the Solid Complex Formulations

Physical stability of the complex Ivacaftor, complex Lumacaftor formulations and pharmaceutical composition was monitored using PAMPA assays. PAMPA permeability was measured in FaSSIF and FeSSIF media after storage of the samples at different conditions. 6 month storage at RT or 40° C./75% relative humidity showed no significant decrease in the measured PAMPA permeability of complex Ivacaftor and complex Lumacaftor under any of the tested condition measured by RP-HPLC (FIG. 8). Pharmaceutical combinations showed stability over 2 months when stored at 40° C./75% relative humidity (FIG. 9).

Structural Analysis

Figure 10:
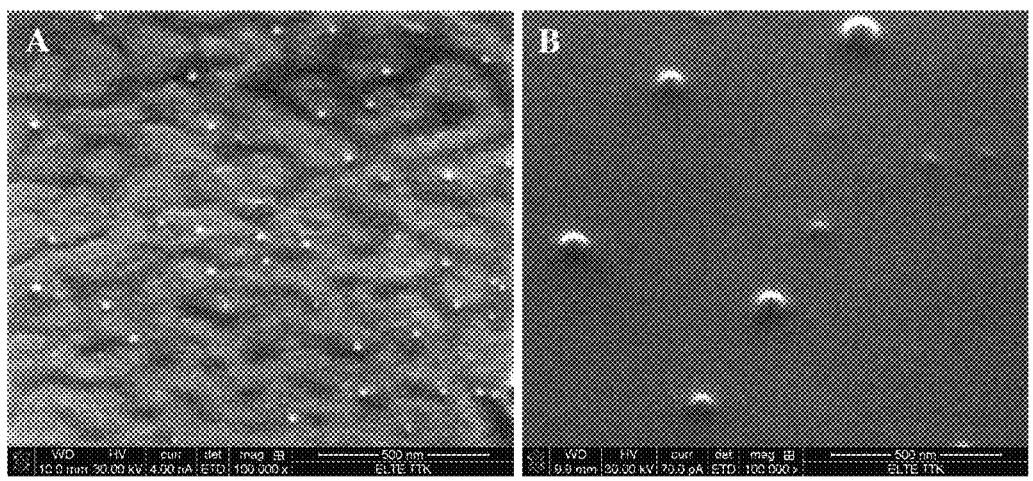
FIG. 10. shows SEM photos of complex Ivacaftor (A) and complex Lumacaftor (B) formulations.

Morphology of complex Ivacaftor formulation and complex Lumacaftor formulation was investigated using FEI Quanta 3D scanning electron microscope. Complex Ivacaftor formulation comprises spherical particles with particle size less than 50 nm, while spherical particles of complex Lumacaftor formulation have particle size in the range of less than 100 nm (FIG. 10).

Structural analysis was performed by using Vertex 70 FT-IR with ATR and HORIBA JobinYvon LabRAM FIR UV-VIS-NIR instruments.

Figure 11:
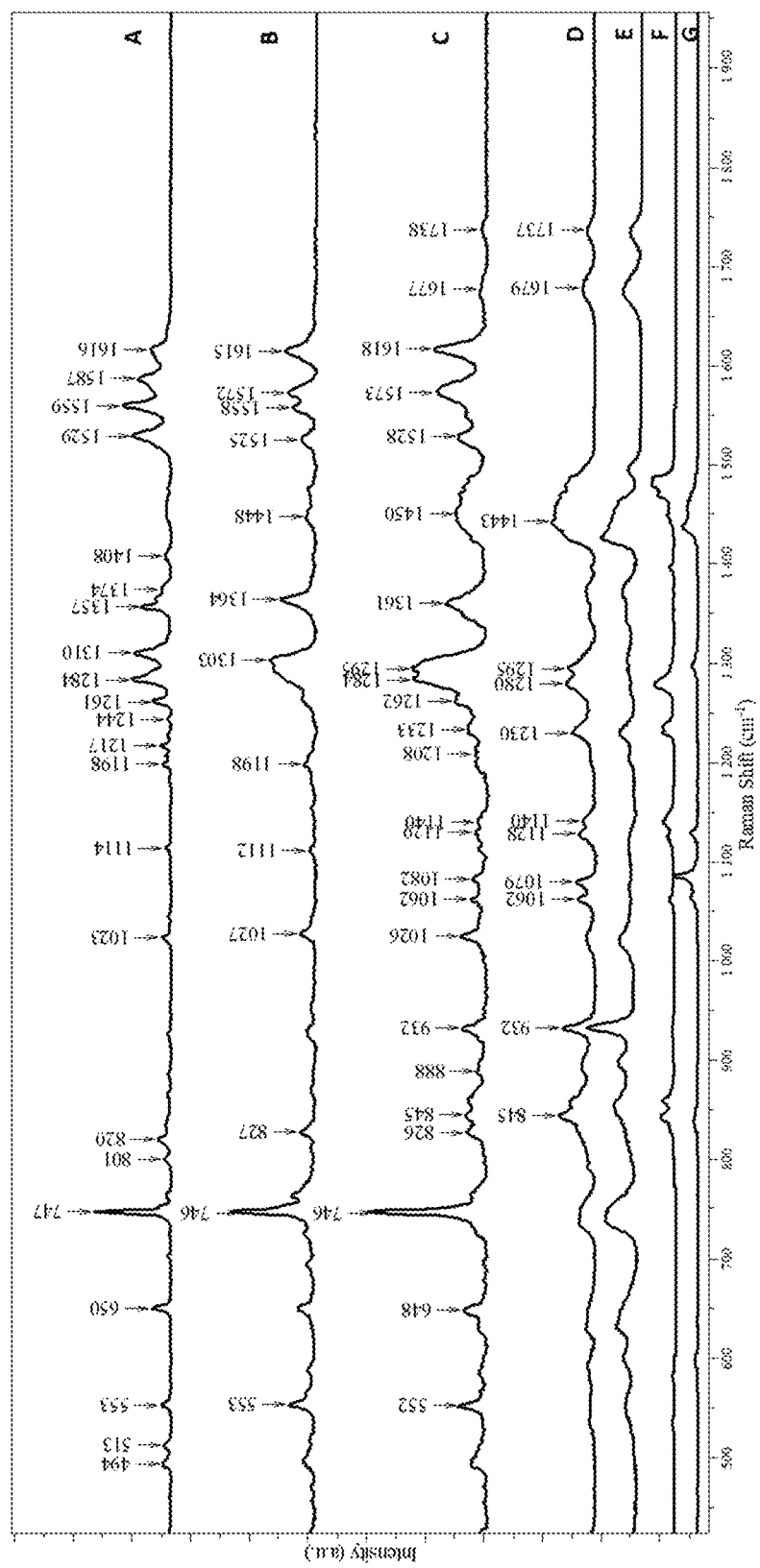
FIG. 11. shows Raman spectra of crystalline Ivacaftor (A), freeze-dried Ivacaftor (B), Complex Ivacaftor formulation (C), Placebo sample (prepared in the absence of Ivacaftor) (D), Luviskol VA64 (E), sodium-lauryl-sulfate (F) and poloxamer (Poloxamer 338-Pluronic F108) Pluronic F108 (G).
Figure 12:
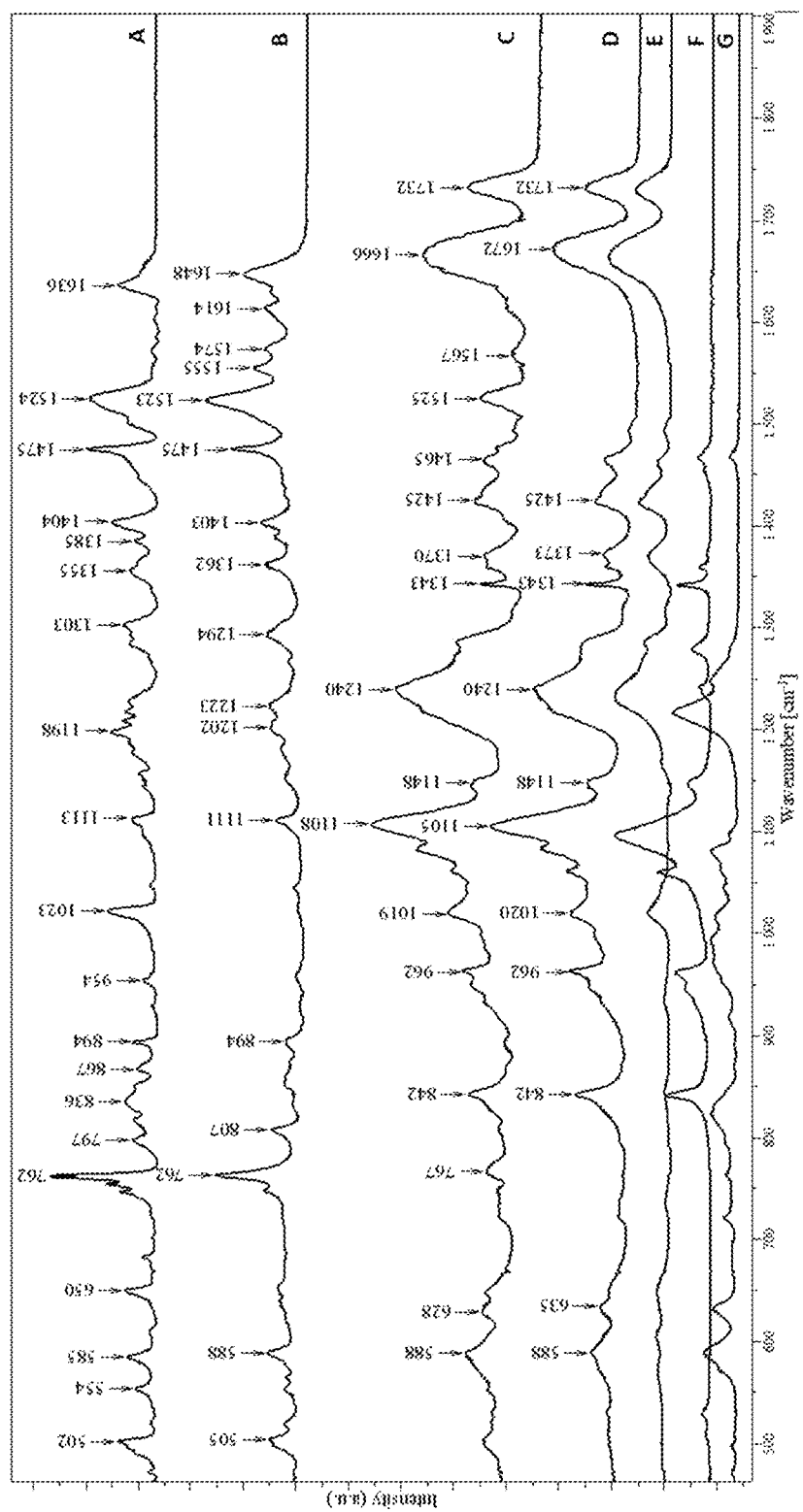
FIG. 12. shows ATR spectra of crystalline Ivacaftor (A), amorphous Ivacaftor (B), complex Ivacaftor formulation (C), placebo (prepared in the lack of Ivacaftor) (D), Luviscol VA64 (E), sodium-lauryl-sulfate (F) and poloxamer (Poloxamer 338-Pluronic F108) Pluronic F108 (G).

Complex Ivacaftor formulation is characterized by the Raman spectrum shown in FIG. 11 and ATR spectrum shown in FIG. 12.

Complex Ivacaftor formulation is characterized by Raman shifts at 552 $cm^{-1}$, 648 $cm^{-1}$, 826 $cm^{-1}$, 845 $cm^{-1}$, 888 $cm^{-1}$, 932 $cm^{-1}$, 1026 $cm^{-1}$, 1062 $cm^{-1}$, 1082 $cm^{-1}$, 1129 $cm^{-1}$, 1140 $cm^{-1}$, 1208 $cm^{-1}$, 1233 $cm^{-1}$, 1262 $cm^{-1}$, 1284 cm$^{-1}$, 1295 cm$^{-1}$, 1361 cm$^{-1}$, 1450 cm$^{-1}$, 1528 cm$^{-1}$, 1573 cm$^{-1}$, 1618 cm$^{-1}$, 1677 cm$^{-1}$, 1738 cm$^{-1}$, 746 cm$^{-1}$, 2884 cm$^{-1}$ and 2936 cm$^{-1}$.

Complex Ivacaftor formulation is characterized by Raman shifts at 1082 cm$^{-1}$, 1233 cm$^{-1}$, 1284 cm$^{-1}$, 1361 cm$^{-1}$, 1528 cm$^{-1}$, 1618 cm$^{-1}$ and 1738 cm$^{-1}$.

Complex Ivacaftor formulation is characterized by infrared (ATR) spectrum having characteristic peaks at 588 cm$^{-1}$, 628 cm$^{-1}$, 767 cm$^{-1}$, 842 cm$^{-1}$, 962 cm$^{-1}$, 1019 cm$^{-1}$, 1108 cm$^{-1}$, 1148 cm$^{-1}$, 1240 cm$^{-1}$, 1343 cm$^{-1}$, 1370 cm$^{-1}$, 1425 cm$^{-1}$, 1465 cm$^{-1}$, 1525 cm$^{-1}$, 1567 cm$^{-1}$, 1666 cm$^{-1}$ and 1732 cm$^{-1}$.

Complex Ivacaftor formulation is characterized by ATR spectrum having characteristic peaks at 628 cm$^{-1}$, 767 cm$^{-1}$, 1108 cm$^{-1}$, 1370 cm$^{-1}$, 1465 cm$^{-1}$ and 1666 cm$^{-1}$.

Figure 13:
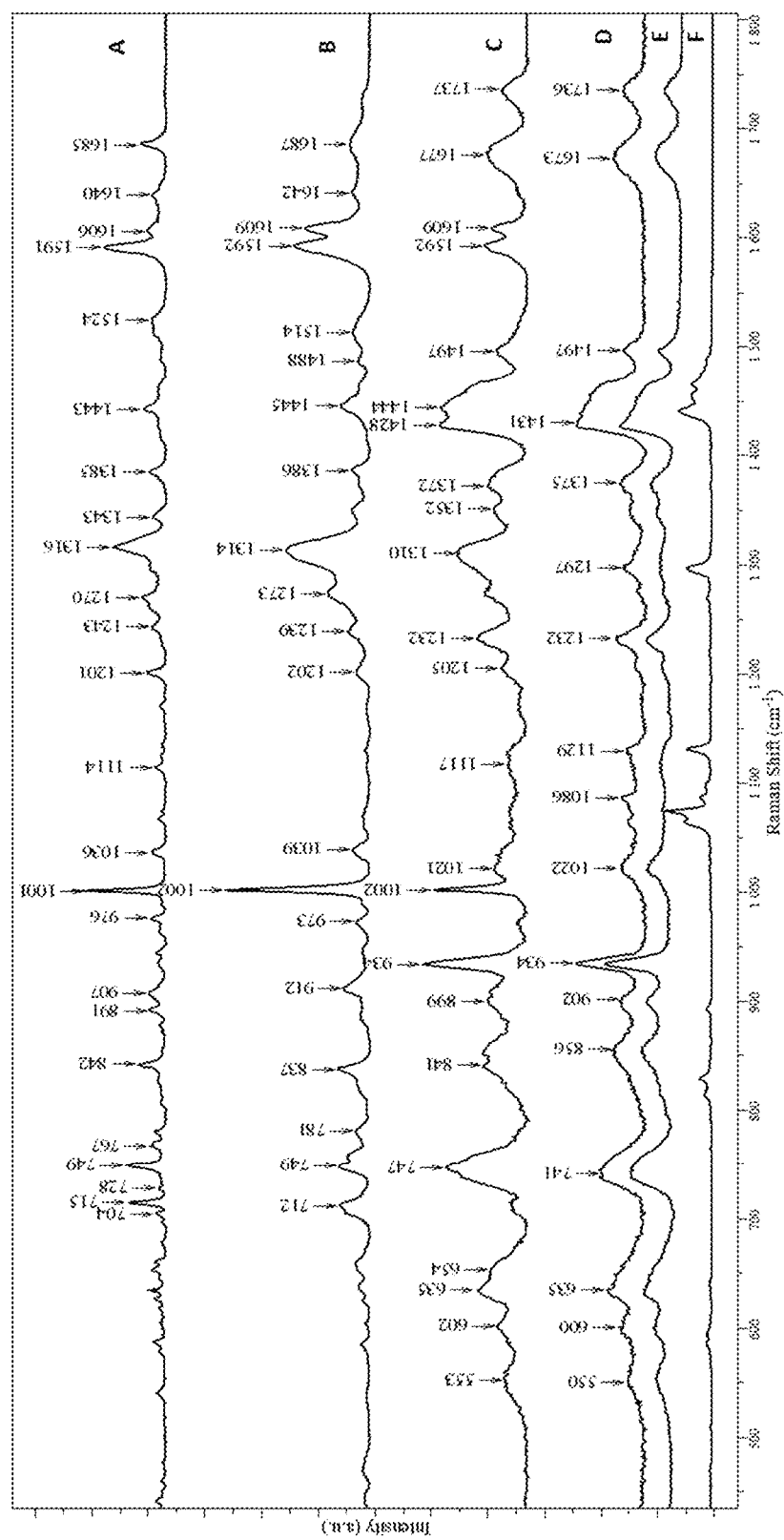
FIG. 13. shows Raman spectra of crystalline Lumacaftor (A), amorphous Lumacaftor (B), complex Lumacaftor formulation (C), placebo (D), Luviscol VA64 (E), SDS (F)
Figure 14:
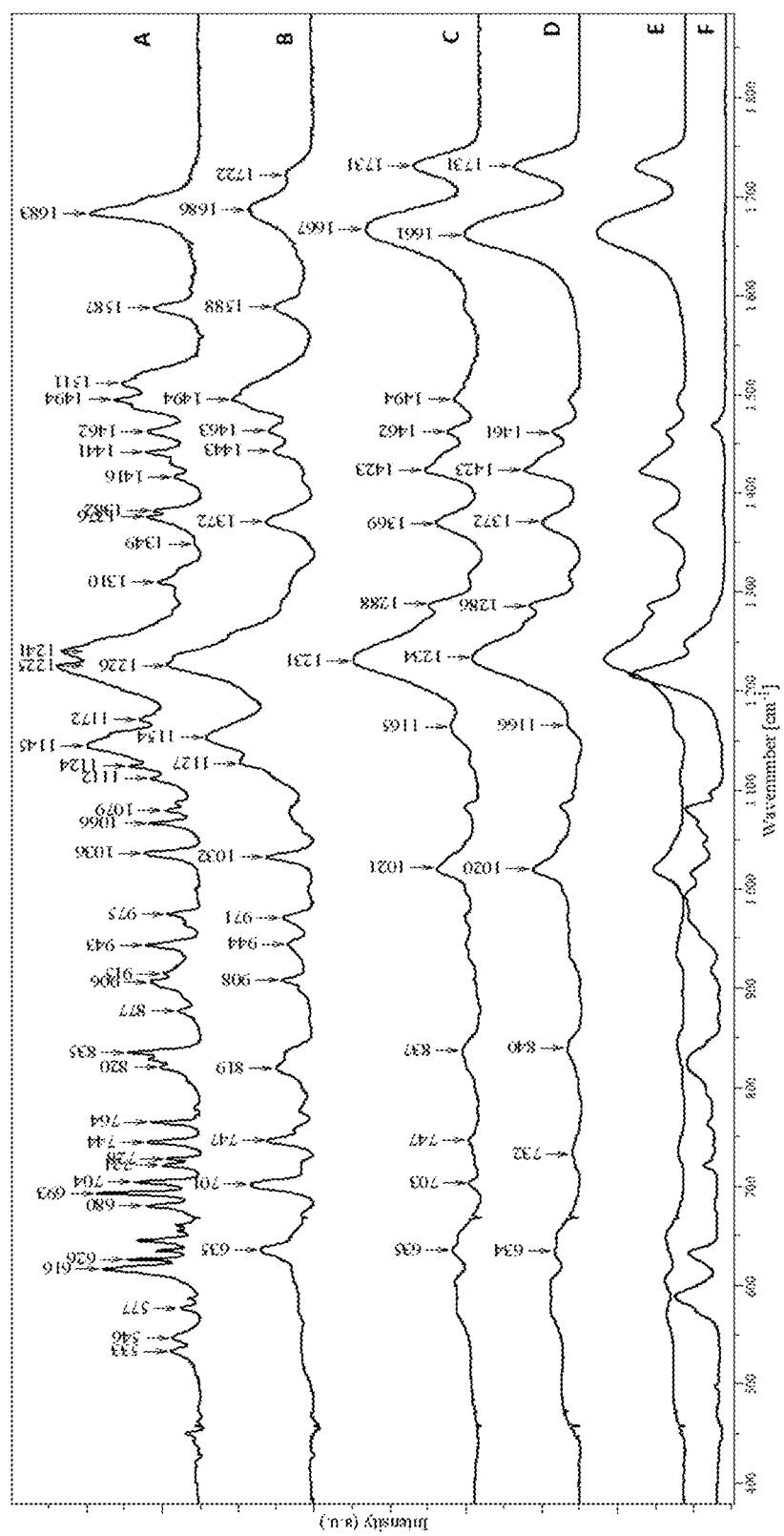
FIG. 14. shows ATR spectra of crystalline Lumacaftor (A), amorphous Lumacaftor (B), complex Lumacaftor formulation (C), placebo (D), Luviscol VA64 (E), SDS (F).

Complex Lumacaftor formulation is characterized by characteristic Raman shifts at 553 cm$^{-1}$, 602 cm$^{-1}$, 635 cm$^{-1}$, 654 cm$^{-1}$, 747 cm$^{-1}$, 841 cm$^{-1}$, 899 cm$^{-1}$, 934 cm$^{-1}$, 1002 cm$^{-1}$, 1021 cm$^{-1}$, 1117 cm$^{-1}$, 1205 cm$^{-1}$, 1232 cm$^{-1}$, 1310 cm$^{-1}$, 1352 cm$^{-1}$, 1372 cm$^{-1}$, 1428 cm$^{-1}$, 1444 cm$^{-1}$, 1497 cm$^{-1}$, 1592 cm$^{-1}$, 1609 cm$^{-1}$ and 1677 cm$^{-1}$ shown in FIG. 13.

Complex Lumacaftor formulation is characterized by characteristic Raman shifts at 553 cm$^{-1}$, 654 cm$^{-1}$, 747 cm$^{-1}$, 841 cm$^{-1}$, 899 cm$^{-1}$, 1117 cm$^{-1}$, 1205 cm$^{-1}$, 1310 cm$^{-1}$, 1372 cm$^{-1}$, 1428 cm$^{-1}$, 1677 cm$^{-1}$ and 1737 cm$^{-1}$.

Complex Lumacaftor formulation is characterized by characteristic infrared (ATR) peaks at 635 cm$^{-1}$, 703 cm$^{-1}$, 747 cm$^{-1}$, 837 cm$^{-1}$, 1021 cm$^{-1}$, 1165 cm$^{-1}$, 1231 cm$^{-1}$, 1288 cm$^{-1}$, 1369 cm$^{-1}$, 1423 cm$^{-1}$, 1462 cm$^{-1}$, 1494 cm$^{-1}$, 1667 cm$^{-1}$ and 1731 cm$^{-1}$ shown in FIG. 1.

Complex Lumacaftor formulation is characterized by characteristic infrared (ATR) peaks at 703 cm$^{-1}$, 837 cm$^{-1}$, 1231 cm$^{-1}$, 1369 cm$^{-1}$ and 1667 cm$^{-1}$.

Figure 15A:
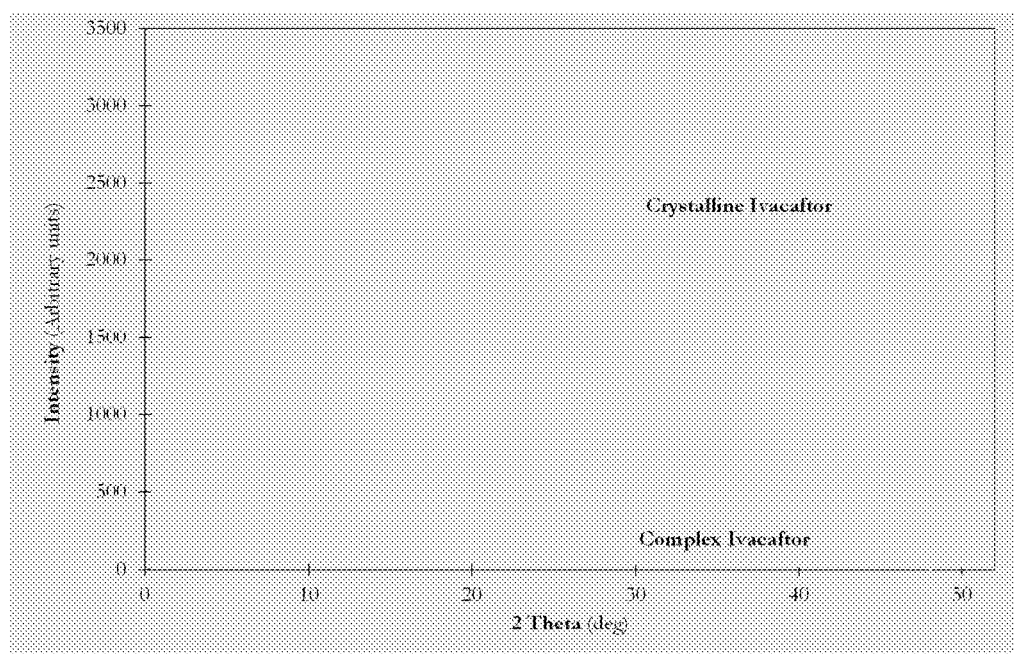
FIG. 15. shows PXRD diffractograms of crystalline Ivacaftor (A, C), complex Ivacaftor formulation (A), crystalline Lumacaftor (B, C) and complex Lumacaftor formulation (B) and Spray-dried complex Ivacaftor and complex Lumacaftor formulations in combination (C)
Figure 15B:
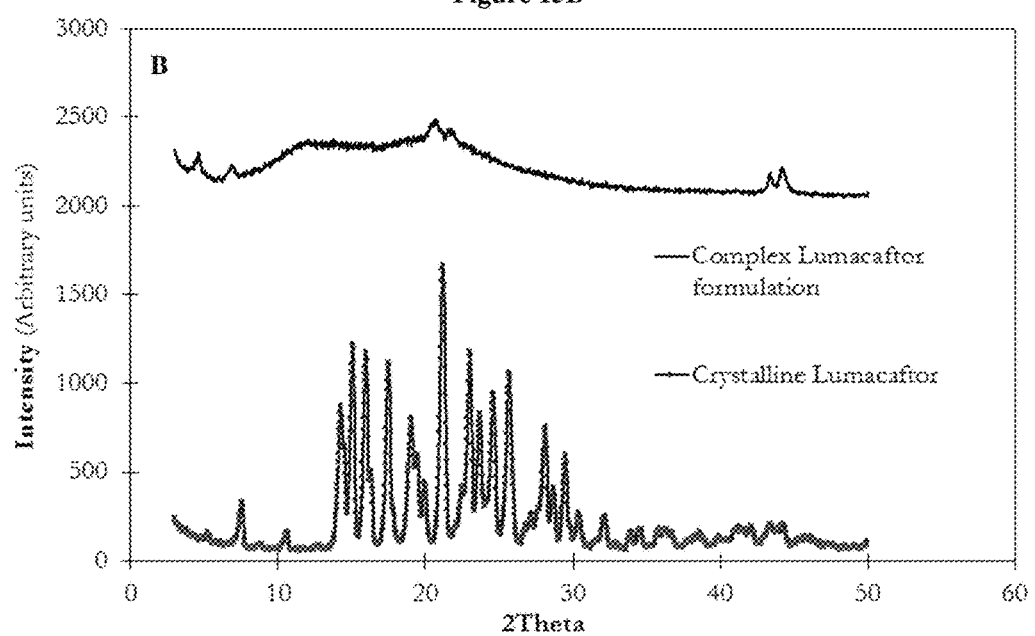
Figure 15C:
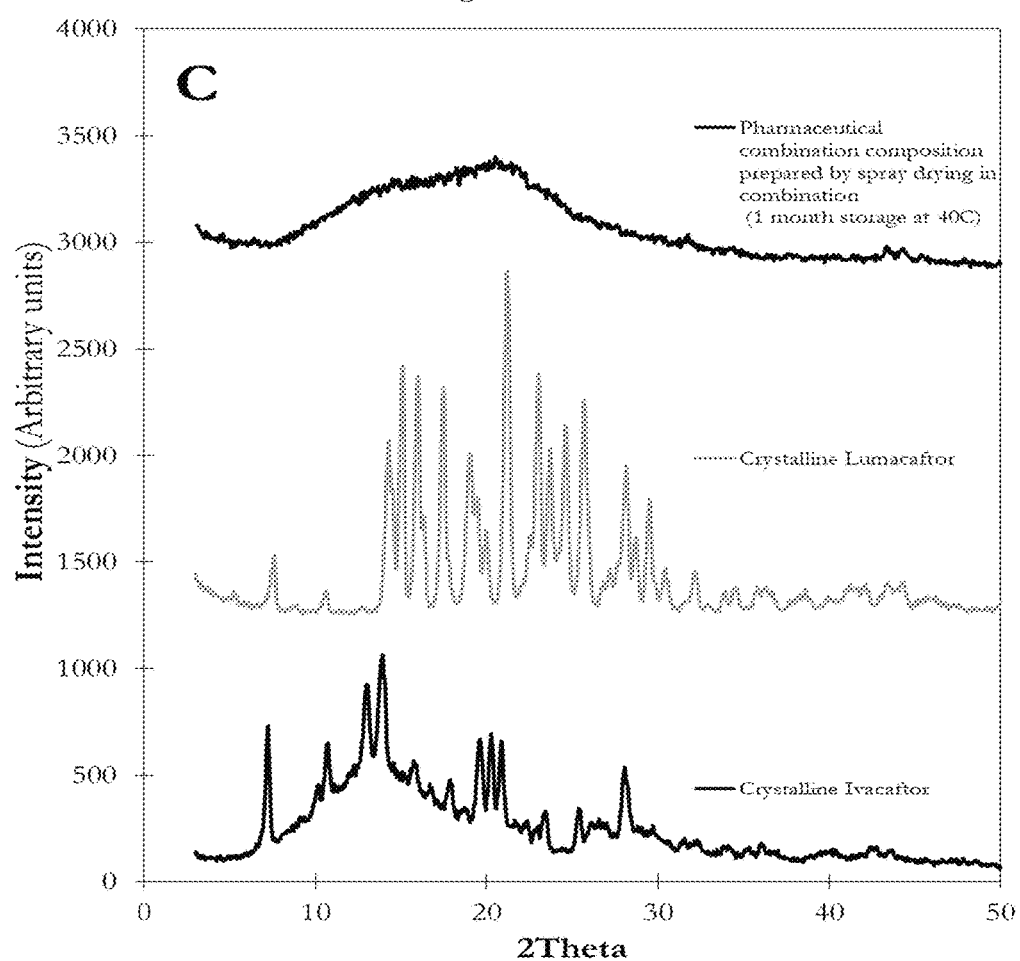

The structure of the complex Ivacaftor, complex Lumacaftor formulation and the pharmaceutical combination compositions were investigated by powder X-ray diffraction (XRD) analysis (Philips PW1050/1870 RTG powder-diffractometer). The measurements showed that both the Ivacaftor and Lumacaftor in the complex and in the combination formulations were XRD amorphous (FIG. 15). Characteristic reflections on the diffractograms at 43 and 44 2Theta could be attributed to sample holder.

Comparative Formulation Study

Ivacaftor is marketed in its solid dispersion form under the trade name of KALYDECO®. Manufacturing of solid dispersion of Ivacaftor is described in US 20140221424 A1 patent application. Using the manufacturing method described in the patent application, solid dispersion of Ivacaftor was prepared for comparative analytical assays. A solvent system of methyl ethyl ketone (MEK) and water in the ratio of 90 wt % MEK:10 wt % water was heated to 20-30° C. in a reaction vessel equipped with a magnetic stirrer and thermal circuit. Into this solvent system, hypromellose acetate succinate polymer (HPMCAS), sodium lauryl sulfate and Ivacaftor were added in the ratio of 19.5 wt % hypromellose acetate succinate:0.5 wt % SLS:80 wt % Ivacaftor. The resulting mixture was solid formulated by spray-drying method.

Comparative analytical assays were used to investigate the physicochemical properties of the formulation prepared by solid dispersion technology and continuous flow mixing.

Figure 16:
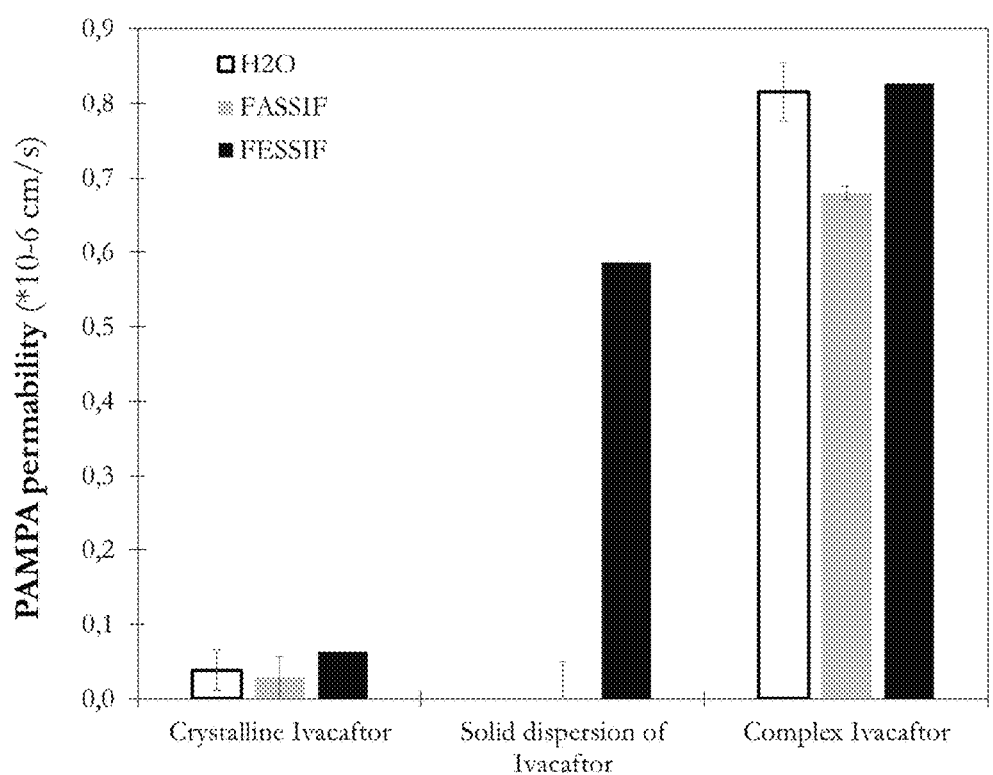
FIG. 16. shows PAMPA permeability of crystalline Ivacaftor, solid dispersion of Ivacaftor and complex Ivacaftor formulation.

PAMPA permeability of the solid dispersion could not be detected in water FaSSIF, while it was 70% of the permeability of the complex Ivacaftor formulation in FeSSIF condition (FIG. 16).

Comparative apparent solubility measurements showed that the apparent solubility of complex Ivacaftor formulation was at least 0.99 mg/mL, while apparent solubility of crystalline Ivacaftor, Ivacaftor in physical mixture, amorphous Ivacaftor in aqueous sodium lauryl sulfate solution and solid dispersion was below 0.1 mg/mL (FIG. 17).

Figure 18:
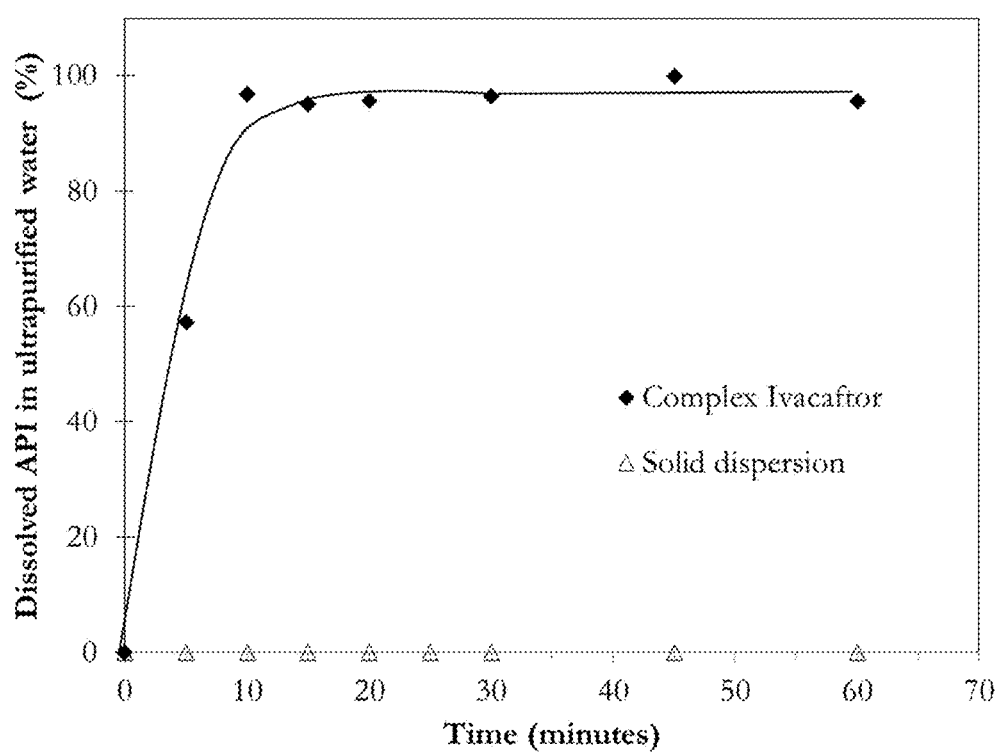
FIG. 18. shows comparative dissolution tests of solid dispersion of Ivacaftor and complex Ivacaftor formulation.

Comparative dissolution tests performed in water showed that the dissolution of Ivacaftor from the granulated complex formulation was instantaneous, within 10 minutes 90% of the Ivacaftor dissolved from the complex Ivacaftor formulation, while 0% Ivacaftor dissolved from the solid dispersion in 60 minutes (FIG. 18).

Ivacaftor was ball milled in the presence of the excipients used for the preparation of solid dispersion. Crystalline Lumacaftor was ball milled in the absence of complexation agent (Luviscol VA64) and pharmaceutically acceptable excipient (SDS) and in the presence of them. Ball milling parameters were the following:

Speed: 500 rpm
Milling time: 1 hour
Number of the balls: 25 pcs with 10 mm diameter
Milling vessel's material: $Si_2N_3$
Quantity of the milled samples: 100 mg API equivalent mass in 12 mL Milli-Q water After the milling, the vessel was washed out with 5 mL Milli-Q water. The products were frozen on salted ice and then it was lyophilized using a freeze-drier equipped with −110° C. ice condenser, with a vacuum pump. The material and in-vitro properties of the resulted formulations were compared to the complex Lumacaftor and Ivacaftor formulations.

Particle size of the formulations was measured by DLS technique in reconstituted dispersion/solution. The results are summarized in FIG. 19. Ball milled crystalline Lumacaftor was hardly redispersible in purified water resulting in a suspension with visible particles, the particle size could not be determined.

Apparent solubility of complex Lumacaftor formulation was 14.913 mg/mL when 20 mg Lumacaftor equivalent formulation was redispersed (FIG. 20).

PAMPA permeability of the formulations was measured in FaSSIF biorelevant media and compared. PAMPA permeability of the complex Lumacaftor formulation was 4.651, while it was 0.288 for the ball milled crystalline Lumacaftor (FIG. 21).

Figure 22:
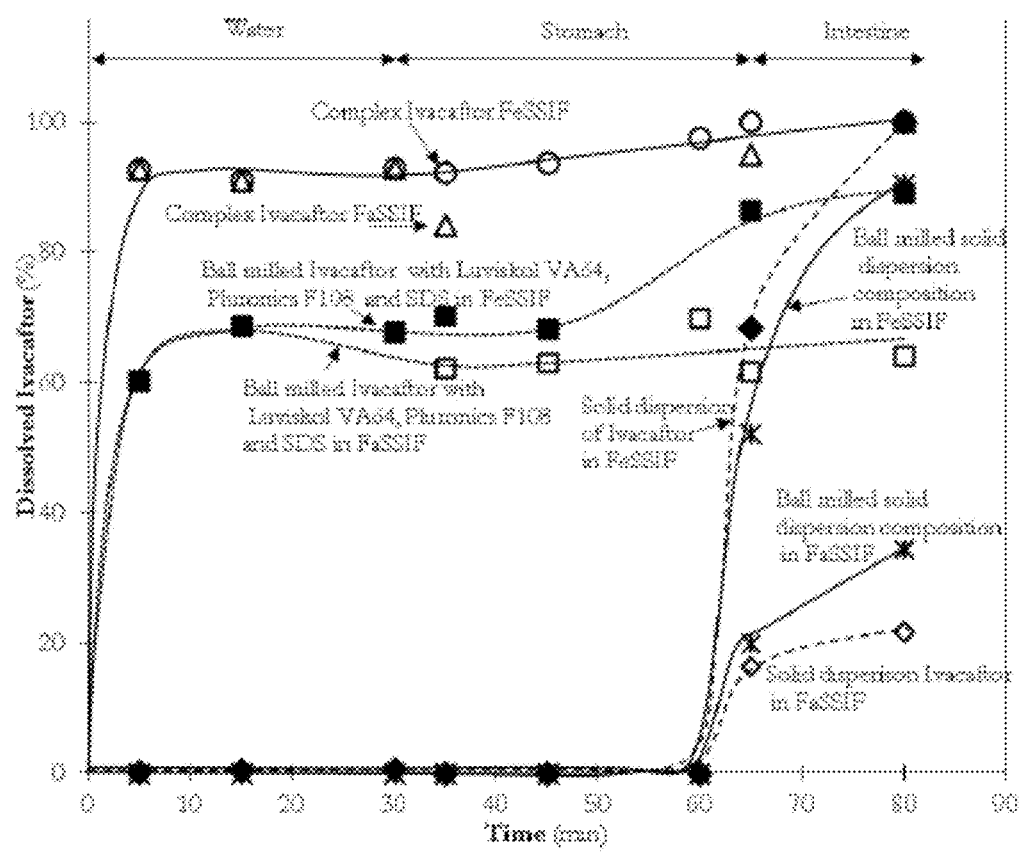
FIG. 22. shows dissolution of Ivacaftor from different pharmaceutical formulations.
Figure 23:
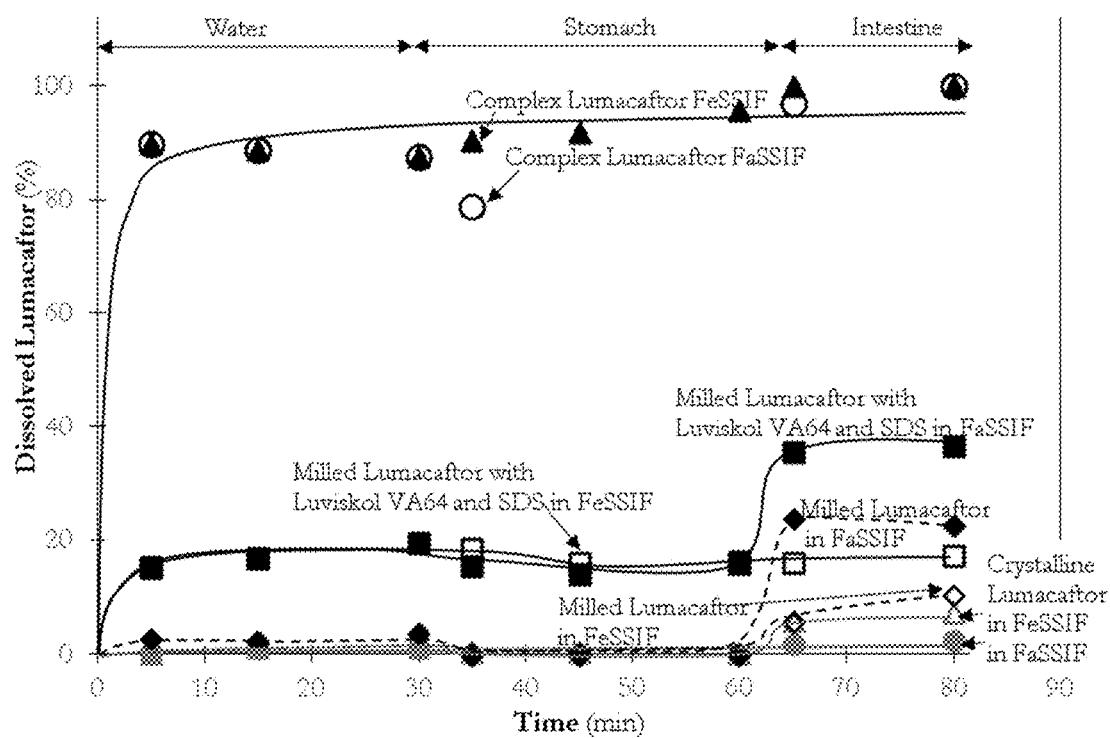
FIG. 23. shows dissolution of Lumacaftor from different pharmaceutical formulations.

GI simulated dissolution of the powder mixture of complex Ivacaftor and Lumacaftor formulations shows completely eliminated food effect both for Ivacaftor and Lumacaftor in in-vitro. Based the dissolution data, significantly increased or full absorption is expected in in-vitro studies. Dissolution of Ivacaftor and Lumacaftor from the powder blend was above 80% within 5 minutes (FIG. 22 and FIG. 23).

In comparison, dissolution of crystalline Ivacaftor showed 5-fold increase in FessiF condition indicating significant different in its absorption in fed state in-vivo. The increase in apparent solubility was 3-fold and 1.5 fold for the ball milled crystalline Ivacaftor and ball milled Ivacaftor with Luviskol VA 64 Pluronic F108 and SDS, respectively. Apparent solubility of Lumacaftor from the crystalline material was below 10% both in FaSSIF and FeSSIF media. The apparent solubility of Lumacaftor increased when the particle size was decreased, however it did not exceed 40% in any of the tested condition. 2-fold difference in apparent solubility was observed in FeSSIF medium compared to the FaSSIF condition (FIG. 22 and FIG. 23).

PAMPA permeabilities of different compositions were measured and compared. PAMPA permeability of complex Ivacaftor and complex Lumacaftor formulation in the pharmaceutical composition outperformed the in-vitro performance of the tested formulations (FIG. 24).

Pharmacokinetics

In-vitro Assays

Based on in-vitro data (FIG. 2, FIG. 3, FIG. 19 and FIG. 20) which shows fast and full dissolution and increased permeability in fasted and fed state simulation it is expected that the complex Lumacaftor formula delivers full absorption and the elimination of the food effect.

In-vivo PK Test in Large Animals

Figure 25:
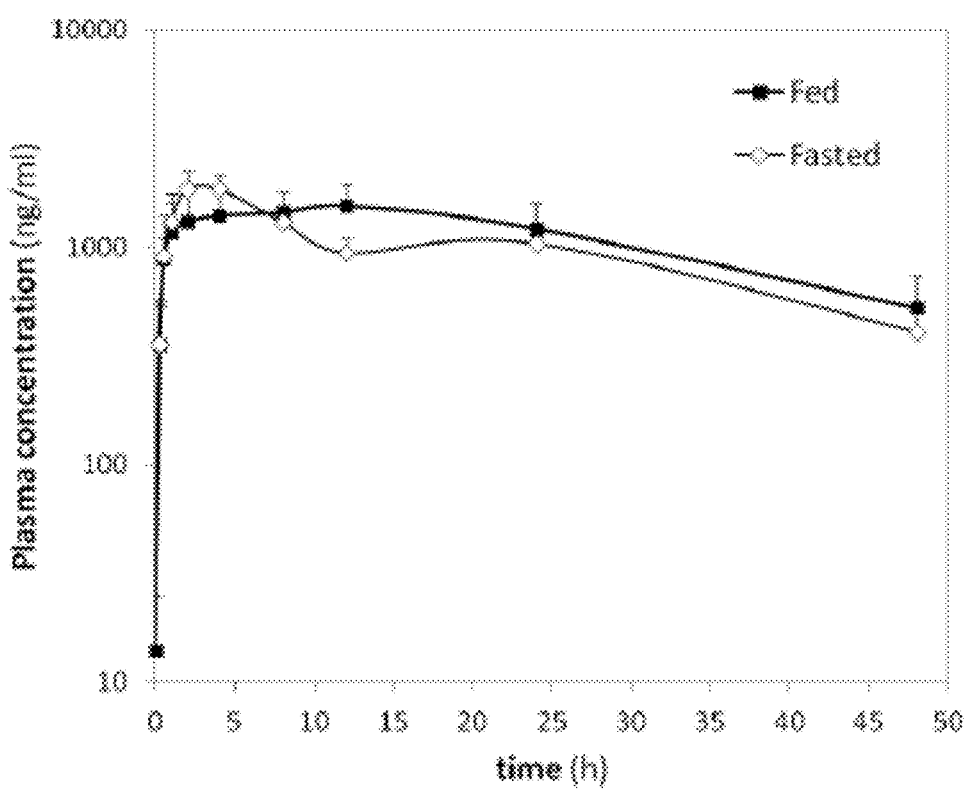
FIG. 25. shows plasma concentrations of Ivacaftor following the oral administration of novel complex in the fasted and in the fed state to beagle dogs at 3 mg/kg dose (N=4).

A beagle dog study using the granulated complex Ivacaftor formulation at a dose of 3 mg/kg was performed in the fasted and fed state. The granulated complex formulation was administered to the animals orally as reconstituted dispersion. Food effect was only 1.1-fold (food effect in humans is 2-4-fold higher in the fed state, that is why the drug has to be taken after a high fat meal). Exposure was 1.25-times higher than the reference exposure. $C_{max}$ was somewhat lower for the complex Ivacaftor formulation, however, for the more important parameter, $C_{24h}$, the complex Ivacaftor was 1.4-times higher (FIG. 25 and FIG. 26).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A binary complex formulation comprising:
   Ivacaftor, or a salt thereof;
   Lumacaftor, or a salt thereof;
   a copolymer of vinylpyrrolidone and vinyl acetate;
   sodium lauryl sulfate, and
   optionally, at least one pharmaceutically acceptable excipient
     wherein said complex formulation has a particle size between 10 nm and 600 nm,
     wherein said complex formulation has a parallel artificial membrane permeability assay (PAMPA) permeability of at least $0.2*10^{-6}$ cm/s for Ivacaftor when dispersed in fasted state simulating intestinal fluid (FaSSIF) or fed state simulating intestinal fluid (FeSSIF) biorelevant media;
     wherein said complex formulation has said PAMPA permeability of at least $0.2*10^{-6}$ cm/s for Lumacaftor when dispersed in FaSSIF or FeSSIF biorelevant media; and wherein said complex formulation is prepared by a spray-drying method, and said PAMPA is stable over time.

2. The complex formulation as recited in claim 1, wherein said complex formulation has a particle size in the range between 10 nm and 400 nm.

3. The complex formulation as recited in claim 1, wherein the complex formulation exhibits X-ray amorphous character in the solid form.

4. The complex formulation as recited in claim 1, wherein said complex formulation comprises 50 to 300 mg Ivacaftor in combination with 25 to 250 mg Lumacaftor.

5. A pharmaceutical combination composition, comprising the complex formulation as recited in claim 1 and one or more pharmaceutically acceptable carriers.

6. The pharmaceutical combination composition as recited in claim 5, wherein said pharmaceutical combination composition is suitable for oral, pulmonary, rectal, colonic, parenteral, intracisternal, intravaginal, intraperitoneal, ocular, otic, local, buccal, nasal, or topical administration.

7. The pharmaceutical combination composition as recited in claim 5, wherein said pharmaceutical combination composition is suitable for oral administration.

8. The pharmaceutical combination composition as recited in claim 7, wherein said pharmaceutical combination composition is in the form of fast dissolving granules.

9. The pharmaceutical combination composition as recited in claim 8, wherein said granules are suitable for the preparation of sachet dosage form.

10. The pharmaceutical combination composition as recited in claim 5, wherein said pharmaceutical combination composition further comprises one or more additional active agents.

11. The pharmaceutical combination composition as recited in claim 10, wherein said additional active agents are chosen from agents used for the treatment of CFTR mediated diseases.

* * * * *